United States Patent
Aronheim

(12) 
(10) Patent No.: US 6,582,927 B2
(45) Date of Patent: Jun. 24, 2003

(54) METHOD FOR DETECTING PROTEIN-PROTEIN INTERACTIONS AND A KIT THEREFOR

(75) Inventor: Ami Aronheim, Binyamina (IL)

(73) Assignees: Rappaport Family Institute for Research in the Medical Sciences, Haifa (IL); Ami Aronheim, Binyamina (IL)

( * ) Notice: Subject to any disclaimer, the term of this patent is extended or adjusted under 35 U.S.C. 154(b) by 0 days.

(21) Appl. No.: 09/765,298

(22) Filed: Jan. 22, 2001

(65) Prior Publication Data

US 2002/0137017 A1 Sep. 26, 2002

Related U.S. Application Data

(63) Continuation of application No. PCT/IL99/00404, filed on Jul. 22, 1999.

(30) Foreign Application Priority Data

Jul. 22, 1998 (IL) .................................................. 125456
Jan. 12, 1999 (IL) .................................................. 128017

(51) Int. Cl.$^7$ ........................ G01N 33/53; C12N 1/14; C12N 1/16; C12N 1/18; C12N 1/00
(52) U.S. Cl. ................. 435/7.2; 435/254.21; 435/320.1; 435/325
(58) Field of Search ........................... 435/6, 4, 254.21, 435/320.1, 325, 23.4, 7.2

(56) References Cited

U.S. PATENT DOCUMENTS 5,776,689 A 7/1998 Karin et al.

OTHER PUBLICATIONS

Aronheim, A. et al., "Isolation of an AP–1 Repressor by a Novel Method for Detecting Protein–Protein Interactions," Mol. Cell. Biol., vol. 17, No. 6, pp. 3094–3102, 1997.

Bhattacharya, S. et al., "Ras membrane targeting is essential for glucose signaling but not for viability in yeast," Proc. Natl. Acad. Sci. USA, vol. 92, pp. 2984–2988, 1995.

Broder, Y. C. et al., "The Ras recruitment system, a novel approach to the study of protein–protein interactions," Current Biology, vol. 8, No. 20, pp. 1121–1124, 1998.

Allen, J. B. et al., "Finding prospective partners in the library: the two–hybrid system and phage display find a match," Trends Biochem. Sci., vol. 20, pp. 511–516, 1995.

Fields, S. et al., "A novel genetic system to detect protein–protein interactios," Nature, vol. 340, pp. 245–246, 1989.

*Primary Examiner*—James Ketter
*Assistant Examiner*—Konstantina T Katcheves
(74) *Attorney, Agent, or Firm*—Oliff & Berridge, PLC

(57) ABSTRACT

A method for detecting an interaction between two tester proteins. In a cell incapable of activating a Ras protein, two nucleic acid sequences are expressed. One sequence encodes for a fusion protein comprising a mutant Ras protein incapable of localizing at the cell membrane and not requiring an exchange factor fused to one of the tester proteins. The other sequence encodes for the other tester protein fused to a plasma membrane localization domain. An interaction between the two fusion proteins leads to the expression of a functional Ras protein that is tested as an altered cell phenotype.

9 Claims, 5 Drawing Sheets

A.

| ADNS | Yes |
|---|---|
| Ras(61)ΔF-Pak | Yes |
| Ras(61)ΔF-Pak | M-GRB2 |
| Ras(61)ΔF-Pak | M-PLCγ2 |
| Ras(61)ΔF-Pak | M-p85(SH3) |
| Ras(61)ΔF-Pak | M-GAP(SH3) |

B.

| ADNS | Yes |
|---|---|
| Ras(61)ΔF-Pak | Rac1 Wt. |
| Ras(61)ΔF-Pak | Rac1 Ac. |
| Ras(61)ΔF-Pak | Rac1 Dn. |

SEQUENCE LISTING

<160> NUMBER OF SEQ ID NOS: 31

<210> SEQ ID NO 1
<211> LENGTH: 435
<212> TYPE: DNA
<213> ORGANISM: Homo sapiens

<400> SEQUENCE: 1

```
tctccagaag aagaagagaa aaggagaatc cgaagggaaa ggaataagat ggctgcagcc    60
aaatgccgca accggaggag ggagctgact gatacactcc aagcggtagg tactctgtgg   120
gttgctcctt tttaaaactt aagggaaagt tggagattga gcataagggc ccttgagtaa   180
gactgtgtct tatgctttcc tttatccctc tgtatacagg agacagacca actagaagat   240
gagaagtctg ctttgcagac cgagattgcc aacctgctga aggagaagga aaaactagag   300
ttcatcctgg cagctcaccg acctgcctgc aagatccctg atgacctggg cttcccagaa   360
gagatgtctg tggcttccct tgatctgact gggggcctgc cagaggttgc caccccggag   420
tctgaggagg ccttc                                                    435
```

<210> SEQ ID NO 2
<211> LENGTH: 107
<212> TYPE: PRT
<213> ORGANISM: Homo sapiens

<400> SEQUENCE: 2

```
Ser Pro Glu Glu Glu Glu Lys Arg Arg Ile Arg Arg Glu Arg Asn Lys
1               5                   10                  15

Met Ala Ala Ala Lys Cys Arg Asn Arg Arg Arg Glu Leu Thr Asp Thr
            20                  25                  30
```

Leu Gln Ala Glu Thr Asp Gln Leu Glu Asp Glu Lys Ser Ala Leu Gln
         35                  40                  45

Thr Glu Ile Ala Asn Leu Leu Lys Glu Lys Glu Lys Leu Glu Phe Ile
         50                  55                  60

Leu Ala Ala His Arg Pro Ala Cys Lys Ile Pro Asp Asp Leu Gly Phe
65                   70                  75                  80

Pro Glu Glu Met Ser Val Ala Ser Leu Asp Leu Thr Gly Gly Leu Pro
                 85                  90                  95

Glu Val Ala Thr Pro Glu Ser Glu Glu Ala Phe
             100                 105

<210> SEQ ID NO 3
<211> LENGTH: 246
<212> TYPE: DNA
<213> ORGANISM: Homo sapiens

<400> SEQUENCE: 3
gcaccaccag agccagtaga agatagaagg cgtgtacgag ctattctacc ttacacaaaa     60
gtaccagaca ctgatgaaat aagtttctta aaaggagata tgttcattgt tcataatgaa    120
ttagaagatg gatggatgtg ggttacaaat ttaagaacag atgaacaagg ccttattgtt    180
gaagacctag tagaagaggt gggccgggaa gaagatccac atgaaggaaa aatatggttc    240
catggg                                                               246

<210> SEQ ID NO 4
<211> LENGTH: 82
<212> TYPE: PRT
<213> ORGANISM: Homo sapiens

<400> SEQUENCE: 4

Ala Pro Pro Glu Pro Val Glu Asp Arg Arg Arg Val Arg Ala Ile Leu
1               5                   10                  15

Pro Tyr Thr Lys Val Pro Asp Thr Asp Glu Ile Ser Phe Leu Lys Gly
             20                  25                  30

Asp Met Phe Ile Val His Asn Glu Leu Glu Asp Gly Trp Met Trp Val
         35                  40                  45

Thr Asn Leu Arg Thr Asp Glu Gln Gly Leu Ile Val Glu Asp Leu Val
     50                  55                  60

Glu Glu Val Gly Arg Glu Glu Asp Pro His Glu Gly Lys Ile Trp Phe
65                  70                  75                  80

His Gly

<210> SEQ ID NO 5
<211> LENGTH: 984
<212> TYPE: DNA
<213> ORGANISM: Homo sapiens

<400> SEQUENCE: 5
atggaagcca tcgccaaata tgacttcaaa gctactgcag acgacgagct gagcttcaaa     60
aggggggaca tcctcaaggt tttgaacgaa gaatgtgatc agaactggta caaggcagag    120
cttaatggaa aagacggctt cattcccaag aactacatag aaatgaaacc acatccgtgg    180
ttttttggca aaatccccag agccaaggca gaagaaatgc ttagcaaaca gcggcacgat    240 ggggccttc ttatccgaga gagtgagagc gctcctgggg acttctccct ctctgtcaag    300
tttgggaacg atgtgcagca cttcaaggtg ctccgagatg gagccgggaa gtacttcctc    360
tgggtggtga agttcaattc tttgaatgag ctggtggatt atcacagatc tacatctgtc    420

-continued

```
tccagaaacc agcagatatt cctgcgggac atagaacagg tgccacagca gccgacatac    480
gtccaggccc tctttgactt tgatccccag gaggatggag agctgggctt ccgccgggga    540
gattttatcc atgtcatgga taactcagac cccaactggt ggaaaggagc ttgccacggg    600
cagaccggca tgtttccccg caattatgtc accccgtga accggaacgt ctaagagtca    660
agaagcaatt atttaaagaa agtgaaaaat gtaaaacaca tacaaaagaa ttaaacccac    720
aagctgcctc tgacagcagc ctgtgaggga gtgcagaaca cctggccggg tcaccctgtg    780
accctctcac tttggttgga actttagggg gtgggagggg gcgttggatt taaaaatgcc    840
aaaacttacc tataaattaa gaagagtttt tattacaaat tttcactgct gctcctcttt    900
cccctccttt gtctttttttt tcatccttttt ttctcttctg tccatcagtg catgacgttt    960
aaggccacgt atagtcctag ctga                                           984
```

<210> SEQ ID NO 6
<211> LENGTH: 217
<212> TYPE: PRT
<213> ORGANISM: Homo sapiens

<400> SEQUENCE: 6

```
Met Glu Ala Ile Ala Lys Tyr Asp Phe Lys Ala Thr Ala Asp Asp Glu
1               5                   10                  15

Leu Ser Phe Lys Arg Gly Asp Ile Leu Lys Val Leu Asn Glu Glu Cys
            20                  25                  30

Asp Gln Asn Trp Tyr Lys Ala Glu Leu Asn Gly Lys Asp Gly Phe Ile
        35                  40                  45

Pro Lys Asn Tyr Ile Glu Met Lys Pro His Pro Trp Phe Phe Gly Lys
    50                  55                  60

Ile Pro Arg Ala Lys Ala Glu Glu Met Leu Ser Lys Gln Arg His Asp
65                  70                  75                  80

Gly Ala Phe Leu Ile Arg Glu Ser Glu Ser Ala Pro Gly Asp Phe Ser
                85                  90                  95

Leu Ser Val Lys Phe Gly Asn Asp Val Gln His Phe Lys Val Leu Arg
            100                 105                 110

Asp Gly Ala Gly Lys Tyr Phe Leu Trp Val Val Lys Phe Asn Ser Leu
        115                 120                 125

Asn Glu Leu Val Asp Tyr His Arg Ser Thr Ser Val Ser Arg Asn Gln
    130                 135                 140

Gln Ile Phe Leu Arg Asp Ile Glu Gln Val Pro Gln Gln Pro Thr Tyr
145                 150                 155                 160

Val Gln Ala Leu Phe Asp Phe Asp Pro Gln Glu Asp Gly Glu Leu Gly
                165                 170                 175

Phe Arg Arg Gly Asp Phe Ile His Val Met Asp Asn Ser Asp Pro Asn
            180                 185                 190

Trp Trp Lys Gly Ala Cys His Gly Gln Thr Gly Met Phe Pro Arg Asn
        195                 200                 205

Tyr Val Thr Pro Val Asn Arg Asn Val
    210                 215
```

<210> SEQ ID NO 7
<211> LENGTH: 552
<212> TYPE: DNA
<213> ORGANISM: Homo sapiens

<400> SEQUENCE: 7

-continued

| | |
|---|---|
| aaataccaac aggatcaagt tgtcaaagaa gataatattg aagctgtagg gaaaaaatta | 60 |
| catgaatata acactcagtt tcaagaaaaa agtcgagaat atgatagatt atatgaagaa | 120 |
| tatacccgca catcccagga aatccaaatg aaaaggacag ctattgaagc atttaatgaa | 180 |
| accataaaaa tatttgaaga acagtgccag acccaagagc ggtacagcaa agaatacata | 240 |
| gaaaagttta acgtgaagg caatgagaaa gaaatacaaa ggattatgca taattatgat | 300 |
| aagttgaagt ctcgaatcag tgaaattatt gacagtagaa gaagattgga agaagacttg | 360 |
| aagaagcagg cagctgagta tcgagaaatt gacaaacgta tgaacagcat taaaccagac | 420 |
| cttatccagc tgagaaagac gagagaccaa tacttgatgt ggttgactca aaaaggtgtt | 480 |
| cggcaaaaga agttgaacga gtggttgggc aatgaaaaca ctgaagacca atattcactg | 540 |
| gtggaagatg at | 552 |

<210> SEQ ID NO 8
<211> LENGTH: 184
<212> TYPE: PRT
<213> ORGANISM: Homo sapiens

<400> SEQUENCE: 8

Lys Tyr Gln Gln Asp Gln Val Val Lys Glu Asp Asn Ile Glu Ala Val
1               5                   10                  15

Gly Lys Lys Leu His Glu Tyr Asn Thr Gln Phe Gln Glu Lys Ser Arg
            20                  25                  30

Glu Tyr Asp Arg Leu Tyr Glu Glu Tyr Thr Arg Thr Ser Gln Glu Ile
        35                  40                  45

Gln Met Lys Arg Thr Ala Ile Glu Ala Phe Asn Glu Thr Ile Lys Ile
    50                  55                  60

Phe Glu Glu Gln Cys Gln Thr Gln Glu Arg Tyr Ser Lys Glu Tyr Ile
65              70                  75                  80

Gly Lys Phe Lys Arg Glu Gly Asn Glu Lys Glu Ile Gln Arg Ile Met
            85                  90                  95

His Asn Tyr Asp Lys Leu Lys Ser Arg Ile Ser Glu Ile Ile Asp Ser
            100                 105                 110

Arg Arg Arg Leu Glu Glu Asp Leu Lys Lys Gln Ala Ala Glu Tyr Arg
        115                 120                 125

Glu Ile Asp Lys Arg Met Asn Ser Ile Lys Pro Asp Leu Ile Gln Leu
    130                 135                 140

Arg Lys Thr Arg Asp Gln Tyr Leu Met Trp Leu Thr Gln Lys Gly Val
145             150                 155                 160

Arg Gln Lys Lys Leu Asn Glu Trp Leu Gly Asn Glu Asn Thr Glu Asp
                165                 170                 175

Gln Tyr Ser Leu Val Glu Asp Asp
            180

<210> SEQ ID NO 9
<211> LENGTH: 2547
<212> TYPE: DNA
<213> ORGANISM: Homo sapiens

<400> SEQUENCE: 9

| | |
|---|---|
| atcgaggagc actgcagcgt ggagcaacag cgtcacatgg ccaaggcctt caaggaagta | 60 |
| tttggcgacc tgctgttgac gaagcccacg gaggccagtg ctgaccagct gccctcgccc | 120 |
| agccagctgc gggagaagat catcatcaag cataagaagc tgggcccccg aggcgatgtg | 180 |
| gatgtcaaca tggaggacaa gaaggacgaa cacaagcaac agggggagct gtacatgtgg | 240 |

-continued

```
gattccattg accagaaatg gactcggcac tactgcgcca ttgctgatgc caagctgtcc      300
ttcagtgatg acattgaaca gactatggag gaggaagtgc cccaggatat accccctaca     360
gaactacatt ttggggagaa atggttccac aagaaggtgg agaagaggac gagtgccgag      420
aagttgctgc aggaatactg catggagacg ggggcaagg atggcacctt cctggttcgg       480
gagagcgaga ccttccccaa tgactacacc ctgtccttct ggcggtcagg ccgggtccag      540
cactgccgga tccgctccac catggagggc gggaccctga aatactactt gactgacaac      600
ctgaggttca ggaggatgta tgccctcatc cagcactacc gcgagacgca cctgccgtgc      660
gccgagttcg agctgcggct cacggaccct gtgcccaacc ccaaccccca cgagtccaag      720
ccgtggtact atgacagcct gagccgcgga gaggcagagg acatgctgat gaggattccc      780
cgggacgggg ccttcctgat ccggaagcga gaggggagcg actcctatgc catcaccttc      840
agggctaggg gcaaggtaaa gcattgtcgc atcaaccggg acggccggca ctttgtgctg      900
gggacctccg cctattttga gagtctggtg gagctcgtca gttactacga gaagcattca     960
ctctaccgaa agatgagact cgctacccc gtgaccccg agctcctgga gcgctacaat       1020
acggaaagag atataaactc cctctacgac gtcagcagaa tgtatgtgga tcccagtgaa     1080
atcaatccgt ccatgcctca gagaaccgtg aaagctctgt atgactacaa agccaagcga    1140
agcgatgagc tgagcttctg ccgtggtgcc ctcatccaca atgtctccaa ggagcccggg     1200
ggctggtgga aggagactta tggaaccagg atccagcagt acttcccatc caactacgtc     1260
gaggacatct caactgcaga cttcgaggag ctagaaaagc agattattga agacaatccc     1320
ttagggtctc tttgcagagg aatattggac ctcaatacct ataacgtcgt gaaagccct     1380 cagggaaaaa accagaagtc ctttgtcttc atcctggagc ccaaggagca gggcgatcct     1440
ccggtggagt ttgccacaga cagggtggag gagctctttg agtggtttca gagcatccga     1500
gagatcacgt ggaagattga cagcaaggag aacaacatga agtactggga agaaccag       1560 tccatcgcca tcgagctctc tgacctggtt gtcactgca aaccaaccag caaaaccaag     1620
gacaacttag aaaatcctga cttccgagaa atccgctcct tgtggagac gaaggctgac      1680 agcatcatca gacagaagcc cgtcgacctc ctgaagtaca tcaaaggg cctgaccgc       1740 gtctacccaa agggacaaag agttgactct tcaaactacg accccttccg cctctggctg    1800
tgcggttctc agatggtggc actcaatttc cagacggcag ataagtacat gcagatgaat     1860
cacgcattgt tttctctcaa cgggcgcacg ggctacgttc tgcagcctga gagcatgagg     1920
acagagaaat atgacccgat gccacccgag tcccagagga agatcctgat gacgctgaca     1980
gtcaaggttc tcggtgctcg ccatctcccc aaacttggac gaagtattgc ctgtccttt     2040 gtagaagtgg agatctgtgg agccgagtat ggcaacaaca agttcaagac gacggttgtg    2100
aatgataatg gcctcagccc tatctgggct ccaacacagg agaaggtgac atttgaaatt     2160
tatgacccaa acctggcatt tctgcgcttt gtggttatg aagaagatat gttcagcgat    2220
cccaactttc ttgctcatgc cacttacccc attaaagcag tcaaatcagg attcaggtcc    2280
gttcctctga agaatgggta cagcgaggac atagagctgg cttccctcct ggttttctgt    2340
gagatgcggc cagtcctgga gagcgaagag gaactttact cctcctgtcg ccagctgagg    2400
aggcggcaag aagaactgaa caaccagctc tttctgtatg acacacacca gaacttgcgc    2460
aatgccaacc gggatgccct ggttaaagag ttcagtgtta atgagaacca ctccagctgt    2520
accaggagaa atgcaacaag aggttaa                                         2547
```

```
<210> SEQ ID NO 10
<211> LENGTH: 847
<212> TYPE: PRT
<213> ORGANISM: Homo sapiens

<400> SEQUENCE: 10

Glu Glu His Cys Ser Val Glu Gln Gln Arg His Met Ala Lys Ala Phe
1               5                   10                  15

Lys Glu Val Phe Gly Asp Leu Leu Thr Lys Pro Thr Glu Ala Ser
            20                  25                  30      Ser

Ala Asp Gln Leu Pro Ser Pro Ser Gln Leu Arg Glu Lys Ile Ile Ile
                35                  40                  45

Lys His Lys Lys Leu Gly Pro Arg Gly Asp Val Asp Val Asn Met Glu
        50                  55                  60

Asp Lys Lys Asp Glu His Lys Gln Gln Gly Glu Leu Tyr Met Trp Asp
65                  70                  75                  80

Ser Ile Asp Gln Lys Trp Thr Arg His Tyr Cys Ala Ile Ala Asp Ala
                85                  90                  95

Lys Leu Ser Phe Ser Asp Ile Glu Gln Thr Met Glu Glu Val
            100                 105                 110

Pro Gln Asp Ile Pro Pro Thr Glu Leu His Phe Gly Glu Lys Trp Phe
            115                 120                 125

His Lys Lys Val Glu Lys Arg Thr Ser Ala Glu Lys Leu Leu Gln Glu
        130                 135                 140

Tyr Cys Met Glu Thr Gly Gly Lys Asp Gly Thr Phe Leu Val Arg Glu
145                 150                 155                 160

Ser Glu Thr Phe Pro Asn Asp Tyr Thr Leu Ser Phe Trp Arg Ser Gly
                165                 170                 175

Arg Val Gln His Cys Arg Ile Arg Ser Thr Met Glu Gly Gly Thr Leu
            180                 185                 190

Lys Tyr Tyr Leu Thr Asp Asn Leu Arg Phe Arg Arg Met Tyr Ala Leu
        195                 200                 205

Ile Gln His Tyr Arg Glu Thr His Leu Pro Cys Ala Glu Phe Glu Leu
        210                 215                 220

Arg Leu Thr Asp Pro Val Pro Asn Pro Asn Pro His Glu Ser Lys Pro
225                 230                 235                 240

Trp Tyr Tyr Asp Ser Leu Ser Arg Gly Glu Ala Glu Asp Met Leu Met
                245                 250                 255

Arg Ile Pro Arg Asp Gly Ala Phe Leu Ile Arg Lys Arg Glu Gly Ser
            260                 265                 270

Asp Ser Tyr Ala Ile Thr Phe Arg Ala Arg Gly Lys Val Lys His Cys
        275                 280                 285

Arg Ile Asn Arg Asp Gly Arg His Phe Val Leu Gly Thr Ser Ala Tyr
    290                 295                 300

Phe Glu Ser Leu Val Glu Leu Val Ser Tyr Tyr Glu Lys His Ser Leu
305                 310                 315                 320

Tyr Arg Lys Met Arg Leu Arg Tyr Pro Val Thr Pro Glu Leu Leu Glu
                325                 330                 335

Arg Tyr Asn Thr Glu Arg Asp Ile Asn Ser Leu Tyr Asp Val Ser Arg
            340                 345                 350

Met Tyr Val Asp Pro Ser Glu Ile Asn Pro Ser Met Pro Gln Arg Thr
        355                 360                 365

Val Lys Ala Leu Tyr Asp Tyr Lys Ala Lys Arg Ser Asp Glu Leu Ser
    370                 375                 380
```

```
Phe Cys Arg Gly Ala Leu Ile His Asn Val Ser Lys Glu Pro Gly Gly
385                 390                 395                 400

Trp Trp Lys Gly Asp Tyr Gly Thr Arg Ile Gln Gln Tyr Phe Pro Ser
            405                 410                 415

Asn Tyr Val Glu Asp Ile Ser Thr Ala Asp Phe Glu Leu Glu Lys
            420                 425                 430

Gln Ile Ile Glu Asp Asn Pro Leu Gly Ser Leu Cys Arg Gly Ile Leu
            435                 440                 445

Asp Leu Asn Thr Tyr Asn Val Val Lys Ala Pro Gln Gly Lys Asn Gln
        450                 455                 460

Lys Ser Phe Val Phe Ile Leu Glu Pro Lys Glu Gln Gly Asp Pro Pro
465                 470                 475                 480

Val Glu Phe Ala Thr Asp Arg Val Glu Glu Leu Phe Glu Trp Phe Gln
                485                 490                 495

Ser Ile Arg Glu Ile Thr Trp Lys Ile Asp Ser Lys Glu Asn Asn Met
            500                 505                 510

Lys Tyr Trp Glu Lys Asn Gln Ser Ile Ala Ile Glu Leu Ser Asp Leu
            515                 520                 525

Val Val Tyr Cys Lys Pro Thr Ser Lys Thr Lys Asp Asn Leu Glu Asn
        530                 535                 540

Pro Asp Phe Arg Glu Ile Arg Ser Phe Val Glu Thr Lys Ala Asp Ser
545                 550                 555                 560

Ile Ile Arg Gln Lys Pro Val Asp Leu Leu Lys Tyr Asn Gln Lys Gly
            565                 570                 575

Leu Thr Arg Val Tyr Pro Lys Gly Gln Arg Val Asp Ser Ser Asn Tyr
            580                 585                 590

Asp Pro Phe Arg Leu Trp Leu Cys Gly Ser Gln Met Val Ala Leu Asn
            595                 600                 605

Phe Gln Thr Ala Asp Lys Tyr Met Gln Met Asn His Ala Leu Phe Ser
            610                 615                 620

Leu Asn Gly Arg Thr Gly Tyr Val Leu Gln Pro Glu Ser Met Arg Thr
625                 630                 635                 640

Glu Lys Tyr Asp Pro Met Pro Pro Glu Ser Gln Arg Lys Ile Leu Met
            645                 650                 655

Thr Leu Thr Val Lys Val Leu Gly Ala Arg His Leu Pro Lys Leu Gly
            660                 665                 670

Arg Ser Ile Ala Cys Pro Phe Val Glu Val Glu Ile Cys Gly Ala Glu
        675                 680                 685

Tyr Gly Asn Asn Lys Phe Lys Thr Thr Val Val Asn Asp Asn Gly Leu
        690                 695                 700

Ser Pro Ile Trp Ala Pro Thr Gln Glu Lys Val Thr Phe Glu Ile Tyr
705                 710                 715                 720

Asp Pro Asn Leu Ala Phe Leu Arg Phe Val Val Tyr Glu Glu Asp Met
                725                 730                 735

Phe Ser Asp Pro Asn Phe Leu Ala His Ala Thr Tyr Pro Ile Lys Ala
            740                 745                 750

Val Lys Ser Gly Phe Arg Ser Val Pro Leu Lys Asn Gly Tyr Ser Glu
            755                 760                 765

Asp Ile Glu Leu Ala Ser Leu Leu Val Phe Cys Glu Met Arg Pro Val
        770                 775                 780

Leu Glu Ser Glu Glu Glu Leu Tyr Ser Ser Cys Arg Gln Leu Arg Arg
785                 790                 795                 800
```

Arg Gln Glu Glu Leu Asn Asn Gln Leu Phe Leu Tyr Asp Thr His Gln
                805                 810                 815

Asn Leu Arg Asn Ala Asn Arg Asp Ala Leu Val Lys Glu Phe Ser Val
            820                 825                 830

Asn Glu Asn His Ser Ser Cys Thr Arg Arg Asn Ala Thr Arg Gly
        835                 840                 845

<210> SEQ ID NO 11
<211> LENGTH: 255
<212> TYPE: DNA
<213> ORGANISM: Homo sapiens

<400> SEQUENCE: 11
atggagtccc aggagcggat caaggcggag aggaagcgca tgaggaaccg catcgctgcc      60
tccaagtgcc gaaaaaggaa gctggagaga atcgcccggc tggaggaaaa agtgaaaacc     120
ttgaaagctc agaactcgga gctggcgtcc acggccaaca tgctcaggga acaggtggca     180
cagcttaaac agaaagtcat gaaccacgtt aacagtgggt gccaactcat gctaacgcag     240
cagttgcaaa cattt                                                      255

<210> SEQ ID NO 12
<211> LENGTH: 85
<212> TYPE: PRT
<213> ORGANISM: Homo sapiens

<400> SEQUENCE: 12

Met Glu Ser Gln Glu Arg Ile Lys Ala Glu Arg Lys Arg Met Arg Asn
1               5                   10                  15

Arg Ile Ala Ala Ser Lys Cys Arg Lys Arg Lys Leu Glu Arg Ile Ala
            20                  25                  30

Arg Leu Glu Glu Lys Val Lys Thr Leu Lys Ala Gln Asn Ser Glu Leu
        35                  40                  45

Ala Ser Thr Ala Asn Met Leu Arg Glu Gln Val Ala Gln Leu Lys Gln
    50                  55                  60

Lys Val Met Asn His Val Asn Ser Gly Cys Gln Leu Met Leu Thr Gln
65                  70                  75                  80

Gln Leu Gln Thr Phe
            85

<210> SEQ ID NO 13
<211> LENGTH: 357
<212> TYPE: DNA
<213> ORGANISM: Homo sapiens

<400> SEQUENCE: 13
gatttccttt tgcccactgg gatttatatc cagttggagg tacctcggga agctaccatt      60
tcttatatta gcagatgtt atggaagcaa gttcacaatt acccaatgtt caacctcctt     120
atggatattg actcctatat gtttgcatgt gtgaatcaga ctgctgtata tgaggagctt     180
gaagatgaaa cacgaagact ctgtgatgtc agaccttttc ttccagttct caaattagtg     240
acaagaagtt gtgacccagg ggaaaaatta gactcaaaaa ttggagtcct tataggaaaa     300
ggtctgcatg aatttgattc cttgaaggat cctgaagtaa atgaatttcg aagaaaa        357

<210> SEQ ID NO 14
<211> LENGTH: 119
<212> TYPE: PRT
<213> ORGANISM: Homo sapiens

```
<400> SEQUENCE: 14

Asp Phe Leu Leu Pro Thr Gly Ile Tyr Ile Gln Leu Glu Val Pro Arg
1               5                   10                  15

Glu Ala Thr Ile Ser Tyr Ile Lys Gln Met Leu Trp Lys Gln Val His
                20                  25                  30

Asn Tyr Pro Met Phe Asn Leu Leu Met Asp Ile Asp Ser Tyr Met Phe
            35                  40                  45

Ala Cys Val Asn Gln Thr Ala Val Tyr Glu Glu Leu Glu Asp Glu Thr
    50                  55                  60

Arg Arg Leu Cys Asp Val Arg Pro Phe Leu Pro Val Leu Lys Leu Val
65                  70                  75                  80

Thr Arg Ser Cys Asp Pro Gly Glu Lys Leu Ser Lys Ile Gly Val
                85                  90                  95

Leu Ile Gly Lys Gly Leu His Glu Phe Asp Ser Leu Lys Asp Pro Glu
                100                 105                 110

Val Asn Glu Phe Arg Arg Lys
                115

<210> SEQ ID NO 15
<211> LENGTH: 639
<212> TYPE: DNA
<213> ORGANISM: Homo sapiens

<400> SEQUENCE: 15
atgtctgata acggagaact ggaagataag cctccagcac ctcctgtgcg aatgagcagc      60
accatcttta gcactggagg caaagaccct ttgtcagcca atcacagttt gaaacctttg     120
ccctctgttc cagaagagaa aaagcccagg cataaaatca tctccatatt ctcaggcaca     180
gagaaaggaa gtaaaagaa agaaaaggaa cggccagaaa tttctcctcc atctgatttt      240
gagcacacca tccatgttgg ctttgatgct gttactggag aattcactgg catgccagaa     300
cagtgggctc gattactaca gacctccaat atcaccaaac tagagcaaaa gaagaatcct     360
caggctgtgc tggatgtcct aaagttctac gactccaaca cagtgaagca gaaatatctg     420
agctttactc ctcctgagaa agatggcctt ccttctggaa cgccagcact gaatgccaag     480
ggaacagaag cacccgcagt agtgacagag gaggaggatg atgatgaaga gactgctcct     540
cccgttattg ccccgcgacc ggatcatacg aaatcaattt acacacggtc tgtaattgac     600
cctgttcctg caccagttgg tgattcacat gttgatggt                           639

<210> SEQ ID NO 16
<211> LENGTH: 213
<212> TYPE: PRT
<213> ORGANISM: Homo sapiens

<400> SEQUENCE: 16

Met Ser Asp Asn Gly Glu Leu Glu Asp Lys Pro Pro Ala Pro Pro Val
1               5                   10                  15

Arg Met Ser Ser Thr Ile Phe Ser Thr Gly Gly Lys Asp Pro Leu Ser
                20                  25                  30

Ala Asn His Ser Leu Lys Pro Leu Pro Ser Val Pro Glu Glu Lys Lys
            35                  40                  45

Pro Arg His Lys Ile Ile Ser Ile Phe Ser Gly Thr Glu Lys Gly Ser
    50                  55                  60

Lys Lys Lys Glu Lys Glu Arg Pro Glu Ile Ser Pro Pro Ser Asp Phe
65                  70                  75                  80
```

```
Glu His Thr Ile His Val Gly Phe Asp Ala Val Thr Gly Glu Phe Thr
                85                  90                  95

Gly Met Pro Glu Gln Trp Ala Arg Leu Leu Gln Thr Ser Asn Ile Thr
            100                 105                 110

Lys Leu Glu Gln Lys Lys Asn Pro Gln Ala Val Leu Asp Val Leu Lys
        115                 120                 125

Phe Tyr Asp Ser Asn Thr Val Lys Gln Lys Tyr Leu Ser Phe Thr Pro
    130                 135                 140

Pro Glu Lys Asp Gly Leu Pro Ser Gly Thr Pro Ala Leu Asn Ala Lys
145                 150                 155                 160

Gly Thr Glu Ala Pro Ala Val Val Thr Glu Glu Asp Asp Glu
                165                 170                 175

Glu Thr Ala Pro Pro Val Ile Ala Pro Arg Pro Asp His Thr Lys Ser
            180                 185                 190

Ile Tyr Thr Arg Ser Val Ile Asp Pro Val Pro Ala Pro Val Gly Asp
        195                 200                 205

Ser His Val Asp Gly
        210
```

<210> SEQ ID NO 17
<211> LENGTH: 800
<212> TYPE: DNA
<213> ORGANISM: Homo sapiens

<400> SEQUENCE: 17

```
ggatccctga aagtgaaaca gaaagtacag catctgcacc aaattctcca agaacaccgt      60
taacacctcc gcctgcttct ggtgcttcca gtaccacaga tgtttgcagt gtatttgatt     120
ccgatcattc gagccctttt cactcaagca atgataccgt ctttatccaa gttactctgc     180
cccatggccc aagatctgct tctgtatcat ctataagttt aaccaaaggc actgatgaag     240
tgcctgtccc tcctcctgtt cctccacgaa gacgaccaga atctgcccca gcagaatctt     300
caccatctaa gattatgtct aagcatttgg acagtccccc agccattcct cctaggcaac     360
ccacatcaaa agcctattca ccacgatatt caatatcaga ccggacctct atctcagacc     420
ctcctgaaag ccctccctta ttaccaccac gagaacctgt gaggacacct gatgttttct     480
caagctcacc actacatctc caacctcccc ctttgggcaa aaaaagtgac catggcaatg     540
ccttcttccc aaacagccct tccccctta caccacctcc tcctcaaaca ccttctcctc     600
acggcacaag aaggcatctg ccatcaccac cattgacaca agaagtggac cttcattcca     660
ttgctgggcc gcctgttcct ccacgacaaa gcacttctca acatatccct aaactccctc     720
caaaaactta caaagggag cacacacacc atccatgca cagagatgga ccaccactgt      780
tggagaatgc ccattcttcc                                                800
```

<210> SEQ ID NO 18
<211> LENGTH: 684
<212> TYPE: PRT
<213> ORGANISM: Homo sapiens

<400> SEQUENCE: 18

```
Ile Pro Glu Pro Glu Pro Thr Glu Ala Asp Arg Ile Ala Ile Glu Asn
1               5                   10                  15

Gly Asp Gln Pro Leu Ser Ala Glu Leu Lys Arg Phe Arg Lys Glu Tyr
            20                  25                  30

Ile Gln Pro Val Gln Leu Arg Val Leu Asn Val Cys Arg His Trp Val
        35                  40                  45
```

```
Glu His His Phe Tyr Asp Phe Glu Arg Asp Ala Tyr Leu Leu Gln Arg
    50                  55                  60

Met Glu Glu Phe Ile Gly Thr Val Arg Gly Lys Ala Met Lys Lys Trp
 65                  70                  75                  80

Val Glu Ser Ile Thr Lys Ile Ile Gln Arg Lys Lys Ile Ala Arg Asp
                 85                  90                  95

Asn Gly Pro Gly His Asn Ile Thr Phe Gln Ser Ser Pro Pro Thr Val
            100                 105                 110

Glu Trp His Ile Ser Arg Pro Gly His Ile Glu Thr Phe Asp Leu Leu
            115                 120                 125

Thr Leu His Pro Ile Glu Ile Ala Arg Gln Leu Thr Leu Leu Glu Ser
    130                 135                 140

Asp Leu Tyr Arg Ala Val Gln Pro Ser Glu Leu Val Gly Ser Val Trp
145                 150                 155                 160

Thr Lys Glu Asp Lys Glu Ile Asn Ser Pro Asn Leu Leu Lys Met Ile
                165                 170                 175

Arg His Thr Thr Asn Leu Thr Leu Trp Phe Glu Lys Cys Ile Val Glu
            180                 185                 190

Thr Glu Asn Leu Glu Glu Arg Val Ala Val Val Ser Arg Ile Ile Glu
            195                 200                 205

Ile Leu Gln Val Phe Gln Glu Leu Asn Asn Phe Asn Gly Val Leu Glu
    210                 215                 220

Val Val Ser Ala Met Asn Ser Ser Pro Val Tyr Arg Leu Asp His Thr
225                 230                 235                 240

Phe Glu Gln Ile Pro Ser Arg Gln Lys Lys Ile Leu Glu Glu Ala His
                245                 250                 255

Glu Leu Ser Glu Asp His Tyr Lys Lys Tyr Leu Ala Lys Leu Arg Ser
            260                 265                 270

Ile Asn Pro Pro Cys Val Pro Phe Gly Ile Tyr Leu Thr Asn Ile
    275                 280                 285

Leu Lys Thr Glu Glu Gly Asn Pro Glu Val Leu Lys Arg His Gly Lys
    290                 295                 300

Glu Leu Ile Asn Phe Ser Lys Arg Arg Lys Val Ala Glu Ile Thr Gly
305                 310                 315                 320

Glu Ile Gln Gln Tyr Gln Asn Gln Pro Tyr Cys Leu Arg Val Glu Ser
                325                 330                 335

Asp Ile Lys Arg Phe Phe Glu Asn Leu Asn Pro Met Gly Asn Ser Met
            340                 345                 350

Glu Lys Glu Phe Thr Asp Tyr Leu Phe Asn Lys Ser Leu Glu Ile Glu
    355                 360                 365

Pro Arg Asn Pro Lys Pro Leu Pro Arg Phe Pro Lys Lys Tyr Ser Tyr
    370                 375                 380

Pro Leu Lys Ser Pro Gly Val Arg Pro Ser Asn Pro Arg Pro Gly Thr
385                 390                 395                 400

Met Arg His Pro Thr Pro Leu Gln Gln Glu Pro Arg Lys Ile Ser Tyr
                405                 410                 415

Ser Arg Ile Pro Glu Ser Glu Thr Glu Ser Thr Ala Ser Ala Pro Asn
            420                 425                 430

Ser Pro Arg Thr Pro Leu Thr Pro Pro Ala Ser Gly Ala Ser Ser
    435                 440                 445

Thr Thr Asp Val Cys Ser Val Phe Asp Ser Asp His Ser Ser Pro Phe
450                 455                 460
```

```
His Ser Ser Asn Asp Thr Val Phe Ile Gln Val Thr Leu Pro His Gly
465                 470                 475                 480

Pro Arg Ser Ala Ser Val Ser Ser Ile Ser Leu Thr Lys Gly Thr Asp
                485                 490                 495

Glu Val Pro Val Pro Pro Val Pro Pro Arg Arg Pro Glu Ser
            500                 505                 510        Ser

Ala Pro Ala Glu Ser Ser Pro Ser Lys Ile Met Ser Lys His Leu Asp
            515                 520                 525

Ser Pro Pro Ala Ile Pro Pro Arg Gln Pro Thr Ser Lys Ala Tyr Ser
    530                 535                 540

Pro Arg Tyr Ser Ile Ser Asp Arg Thr Ser Ile Ser Asp Pro Pro Glu
545                 550                 555                 560

Ser Pro Pro Leu Leu Pro Pro Arg Glu Pro Val Arg Thr Pro Asp Val
                565                 570                 575

Phe Ser Ser Ser Pro Leu His Leu Gln Pro Pro Leu Gly Lys Lys
                580                 585                 590

Ser Asp His Gly Asn Ala Phe Phe Pro Asn Ser Pro Ser Pro Phe Thr
                595                 600                 605

Pro Pro Pro Pro Gln Thr Pro Ser Pro His Gly Thr Arg Arg His Leu
    610                 615                 620

Pro Ser Pro Pro Leu Thr Gln Glu Val Asp Leu His Ser Ile Ala Gly
625                 630                 635                 640

Pro Pro Val Pro Pro Arg Gln Ser Thr Ser Gln His Ile Pro Lys Leu
                645                 650                 655

Pro Pro Lys Thr Tyr Lys Arg Glu His Thr His Pro Ser Met His Arg
            660                 665                 670

Asp Gly Pro Pro Leu Leu Glu Asn Ala His Ser Ser
            675                 680

<210> SEQ ID NO 19
<211> LENGTH: 87
<212> TYPE: DNA
<213> ORGANISM: Homo sapiens

<400> SEQUENCE: 19
atggggagta gcaagagcaa gcctaaggac cccagccagc gccggcccgg gagatccact   60
agtaacggcc gccagtgtgc tggaatt                                       87

<210> SEQ ID NO 20
<211> LENGTH: 29
<212> TYPE: PRT
<213> ORGANISM: Homo sapiens

<400> SEQUENCE: 20

Met Gly Ser Ser Lys Ser Lys Pro Lys Asp Pro Ser Gln Arg Arg Pro
1               5                   10                  15

Gly Arg Ser Thr Ser Asn Gly Arg Gln Cys Ala Gly Ile
            20                  25

<210> SEQ ID NO 21
<211> LENGTH: 576
<212> TYPE: DNA
<213> ORGANISM: Homo sapiens

<400> SEQUENCE: 21
atgcagacaa ttaagtgtgt tgttgtgggc gatggtgctg ttggtaaaac atgtctcctg   60
atatcctaca caacaaacaa atttccatcg gaatatgtac cgactgtttt tgacaactat   120
```

```
gcagtcacag ttatgattgg tggagaacca tatactcttg acttttttga tactgcaggg    180
caagaggatt atgacagatt acgaccgctg agttatccac aaacagatgt atttctagtc    240 tgttttttcag tggtctctcc atcttcattt gaaaacgtga agaaaagtg ggtgcctgag    300 ataactcacc actgtccaaa gactcctttc ttgcttgttg ggactcaaat tgatctcaga    360
gatgacccct ctactattga gaaacttgcc aagaacaaac agaagcctat cactccagag    420
actgctgaaa agctggcccg tgacctgaag gctgtcaagt atgtggagtg ttctgcactt    480
acacagaaag gcctaaagaa tgtatttgac gaagcaatat tggctgccct ggagcctcca    540
gaaccgaaga gagccgcag gtgtgtgctg ctatga                              576

<210> SEQ ID NO 22
<211> LENGTH: 191
<212> TYPE: PRT
<213> ORGANISM: Homo sapiens

<400> SEQUENCE: 22

Met Gln Thr Ile Lys Cys Val Val Gly Asp Gly Ala Val Gly Lys
1               5                  10                  15

Thr Cys Leu Leu Ile Ser Tyr Thr Thr Asn Lys Phe Pro Ser Glu Tyr
                20                  25                  30

Val Pro Thr Val Phe Asp Asn Tyr Ala Val Thr Val Met Ile Gly Gly
                35                  40                  45

Glu Pro Tyr Thr Leu Gly Leu Phe Asp Thr Ala Gly Gln Glu Asp Tyr
        50                  55                  60

Asp Arg Leu Arg Pro Leu Ser Tyr Pro Gln Thr Asp Val Phe Leu Val
65                  70                  75                  80

Cys Phe Ser Val Val Ser Pro Ser Ser Phe Glu Asn Val Lys Glu Lys
                85                  90                  95

Trp Val Pro Glu Ile Thr His His Cys Pro Lys Thr Pro Phe Leu Leu
                100                 105                 110

Val Gly Thr Gln Ile Asp Leu Arg Asp Asp Pro Ser Thr Ile Glu Lys
                115                 120                 125

Leu Ala Lys Asn Lys Gln Lys Pro Ile Thr Pro Glu Thr Ala Glu Lys
        130                 135                 140

Leu Ala Arg Asp Leu Lys Ala Val Lys Tyr Val Glu Cys Ser Ala Leu
145                 150                 155                 160

Thr Gln Lys Gly Leu Lys Asn Val Phe Asp Glu Ala Ile Leu Ala Ala
                165                 170                 175

Leu Glu Pro Pro Glu Pro Lys Lys Ser Arg Arg Cys Val Leu Leu
                180                 185                 190

<210> SEQ ID NO 23
<211> LENGTH: 576
<212> TYPE: DNA
<213> ORGANISM: Homo sapiens

<400> SEQUENCE: 23
atgcaggcca tcaagtgtgt ggtggtggga gacggagctg taggtaaaac ttgcctactg     60
atcagttaca aaccaatgc atttcctgga gaatatatcc ctactgtctt tgacaattat    120
tctgccaatg ttatggtaga tggaaaaccg gtgaatctgg gcttatggga tacagctgga    180
caagaagatt atgacagatt acgccccta tcctatccgc aaacagatgt gttcttaatt    240
tgcttttccc ttgtgagtcc tgcatcattt gaaaatgtcc gtgcaaagtg gtatcctgag    300
```

-continued

```
gtgcggcacc actgtcccaa cactcccatc atcctagtgg gaactaaact tgatcttagg        360
gatgataaag acacgatcga gaaactgaag gagaagaagc tgactcccat cacctatccg        420
cagggtctag ccatggctaa ggagattggt gctgtaaaat acctggagtg ctcggcgctc        480
acacagcgag gcctcaagac agtgtttgac gaagcgatcc gagcagtcct ctgcccgcct        540
cccgtgaaga agaggaagag aaaatgcctg ttgtag                                  576
```

<210> SEQ ID NO 24
<211> LENGTH: 191
<212> TYPE: PRT
<213> ORGANISM: Homo sapiens

<400> SEQUENCE: 24

```
Met Gln Ala Ile Lys Cys Val Val Gly Asp Gly Ala Val Gly Lys
1               5                   10                  15

Thr Cys Leu Leu Ile Ser Tyr Thr Thr Asn Ala Phe Pro Gly Glu Tyr
                20                  25                  30

Ile Pro Thr Val Phe Asp Asn Tyr Ser Ala Asn Val Met Val Asp Gly
                35                  40                  45

Lys Pro Val Asn Leu Gly Leu Trp Asp Thr Ala Gly Gln Glu Asp Tyr
        50                  55                  60

Asp Arg Leu Arg Pro Leu Ser Tyr Pro Gln Thr Asp Val Phe Leu Ile
65                  70                  75                  80

Cys Phe Ser Leu Val Ser Pro Ala Ser Phe Glu Asn Val Arg Ala Lys
                85                  90                  95

Trp Tyr Pro Glu Val Arg His His Cys Pro Asn Thr Pro Ile Ile Leu
                100                 105                 110

Val Gly Thr Lys Leu Asp Leu Arg Asp Asp Lys Asp Thr Ile Glu Lys
                115                 120                 125

Leu Lys Glu Lys Lys Leu Thr Pro Ile Thr Tyr Pro Gln Gly Leu Ala
        130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Pro Val Lys Lys Arg Lys Arg Lys Cys Leu Leu
                180                 185                 190
```

<210> SEQ ID NO 25
<211> LENGTH: 551
<212> TYPE: DNA
<213> ORGANISM: Homo sapiens

<400> SEQUENCE: 25

```
gaatataagc tggtggtggt gggcgccggc ggtgtgggca agagtgcgct gaccatccag         60
ctgatccaga accattttgt ggacgaatac gaccccacta tagaggattc ctaccggaag        120
caggtggtca ttgatgggga cgtgcctgt tggacatcc tggataccgc cggccaggag         180
gagtacagcg ccatgcggga ccagtacatg cgcaccgggg agggcttcct gtgtgtgttt        240
gccatcaaca acaccaagtc ttttgaggac atccaccagt acagggagca gatcaaacgg        300
gtgaaggact cggatgacgt gcccatggtg ctggtgggga caagtgtga cctggctgca        360 cgcactgtgg aatctcggca ggctcaggac ctcgcccgaa gctacggcat cccctacatc        420
gagacctcgg ccaagaccg gcaggagtg gaggatgcct tctacacgtt ggtgcgtgag         480
atccggcagc acaagctgcg gaagctgaac cctcctgatg agagtggccc cggctgcatg        540
```
agctgcaagt g                                                        551

<210> SEQ ID NO 26
<211> LENGTH: 183
<212> TYPE: PRT
<213> ORGANISM: Homo sapiens

<400> SEQUENCE: 26

Glu Tyr Lys Leu Val Val Gly Ala Gly Gly Val Gly Lys Ser Ala
1               5                   10                  15

Leu Thr Ile Gln Leu Ile Gln Asn His Phe Val Asp Glu Tyr Asp Pro
            20                  25                  30

Thr Ile Glu Asp Ser Tyr Arg Lys Gln Val Val Ile Asp Gly Glu Thr
        35                  40                  45

Cys Leu Leu Asp Ile Leu Asp Thr Ala Gly Gln Glu Glu Tyr Ser Ala
    50                  55                  60

Met Arg Asp Gln Tyr Met Arg Thr Gly Glu Gly Phe Leu Cys Val Phe
65                  70                  75                  80

Ala Ile Asn Asn Thr Lys Ser Phe Glu Asp Ile His Gln Tyr Arg Glu
                85                  90                  95

Gln Ile Lys Arg Val Lys Asp Ser Asp Asp Val Pro Met Val Leu Val
            100                 105                 110

Gly Asn Lys Cys Asp Leu Ala Ala Arg Thr Val Glu Ser Arg Gln Ala
        115                 120                 125

Gln Asp Leu Ala Arg Ser Tyr Gly Ile Pro Tyr Ile Glu Thr Ser Ala
    130                 135                 140

Lys Thr Arg Gln Gly Val Glu Asp Ala Phe Tyr Thr Leu Val Arg Glu
145                 150                 155                 160

Ile Arg Gln His Lys Leu Arg Lys Leu Asn Pro Pro Asp Glu Ser Gly
                165                 170                 175

Pro Gly Cys Met Ser Cys Lys
            180

<210> SEQ ID NO 27
<211> LENGTH: 570
<212> TYPE: DNA
<213> ORGANISM: Homo sapiens

<400> SEQUENCE: 27
atgacggaat ataagctggt ggtggtgggc gccggcggtg tgggcaagag tgcgctgacc      60
atccagctga tccagaacca tttttgtggac gaatacgacc ccactataga ggattcctac    120
cggaagcagg tggtcattga tggggagacg tgcctgttgg acatcctgga taccgccggc    180
ctggaggagt acagcgccat gcgggaccag tacatgcgca ccggggaggg cttcctgtgt    240
gtgtttgcca tcaacaacac caagtctttt gaggacatcc accagtacag ggagcagatc    300
aaacgggtga aggactcgga tgacgtgccc atggtgctgg tggggaacaa gtgtgacctg    360
gctgcacgca ctgtggaatc tcggcaggct caggacctcg cccgaagcta cggcatcccc    420
tacatcgaga cctcggccaa gacccggcag ggagtggagg atgccttcta cacgttggtg    480
cgtgagatcc ggcagcacaa gctgcggaag ctgaaccctc tgatgagag tggccccggc    540 tgcatgagct gcaagtgtgt gctctcctga                                      570

<210> SEQ ID NO 28
<211> LENGTH: 183
<212> TYPE: PRT

<213> ORGANISM: Homo sapiens

<400> SEQUENCE: 28

```
Glu Tyr Lys Leu Val Val Gly Ala Gly Gly Val Gly Lys Ser Ala
1               5                   10                  15

Leu Thr Ile Gln Leu Ile Gln Asn His Phe Val Asp Glu Tyr Asp Pro
            20                  25                  30

Thr Ile Glu Asp Ser Tyr Arg Lys Gln Val Val Ile Asp Gly Glu Thr
        35                  40                  45

Cys Leu Leu Asp Ile Leu Asp Thr Ala Gly Leu Glu Glu Tyr Ser Ala
    50                  55                  60

Met Arg Asp Gln Tyr Met Arg Thr Gly Glu Gly Phe Leu Cys Val Phe
65                  70                  75                  80

Ala Ile Asn Asn Thr Lys Ser Phe Glu Asp Ile His Gln Tyr Arg Glu
                85                  90                  95

Gln Ile Lys Arg Val Lys Asp Ser Asp Asp Val Pro Met Val Leu Val
            100                 105                 110

Gly Asn Lys Cys Asp Leu Ala Ala Arg Thr Val Glu Ser Arg Gln Ala
        115                 120                 125

Gln Asp Leu Ala Arg Ser Tyr Gly Ile Pro Tyr Ile Glu Thr Ser Ala
    130                 135                 140

Lys Thr Arg Gln Gly Val Glu Asp Ala Phe Tyr Thr Leu Val Arg Glu
145                 150                 155                 160

Ile Arg Gln His Lys Leu Arg Lys Leu Asn Pro Pro Asp Glu Ser Gly
                165                 170                 175

Pro Gly Cys Met Ser Cys Lys
            180
```

<210> SEQ ID NO 29
<211> LENGTH: 8001
<212> TYPE: DNA
<213> ORGANISM: Homo sapiens

<400> SEQUENCE: 29

| | | | | | | |
|---|---|---|---|---|---|---|
| aagcttctag | acccgggggc | accggatccc | catggcccgg | gcgacgtcga | cgcgcgcacg | 60 |
| cgtgagctcg | cggccgccgc | ggttaattaa | ttaattaacc | gcggccttttt | tggccagctc | 120 |
| gaattcactg | gccgtcgttt | tacaacgtcg | tgactgggaa | aaccctggcg | ttacccaact | 180 |
| taatcgcctt | gcagcacatc | ccctttcgc | cagagctttg | gacttcttcg | ccagaggttt | 240 |
| ggtcaagtct | ccaatcaagg | ttgtcggctt | gtctaccttg | ccagaaattt | acgaaaagat | 300 |
| ggaaaagggt | caaatcgttg | gtagatacgt | tgttgacact | tctaaataag | cgaatttctt | 360 |
| atgatttatg | attttttatta | ttaaataagt | tataaaaaaa | ataagtgtat | acaaatttta | 420 |
| aagtgactct | taggttttaa | aacgaaaatt | cttattcttg | agtaactctt | tcctgtaggt | 480 |
| caggttgctt | tctcaggtat | agcatgaggt | cgctcttatt | gaccacacct | ctaccggcat | 540 |
| gccgagcaaa | tgcctgcaaa | tcgctccca | tttcacccaa | ttgtagatat | gctaactcca | 600 |
| gcaatgagtt | gatgaatctc | ggtgtgtatt | ttatgtcctc | agaggacaac | acctgttgta | 660 |
| atcgttcttc | cacacggatc | gatcctgcat | taatgaatcg | gccaacgcgc | ggggagaggc | 720 |
| ggtttgcgta | ttgggcgctc | ttccgcttcc | tcgctcactg | actcgctgcg | ctcggtcgtt | 780 |
| cggctgcggc | gagcggtatc | agctcactca | aaggcggtaa | tacggttatc | cacagaatca | 840 |
| ggggataacg | caggaaagaa | catgtgagca | aaaggccagc | aaaaggccag | gaaccgtaaa | 900 |
| aaggccgcgt | tgctggcgtt | tttccatagg | ctccgccccc | ctgacgagca | tcacaaaaat | 960 |

-continued

```
cgacgctcaa gtcagaggtg gcgaaacccg acaggactat aaagatacca ggcgtttccc    1020
cctggaagct ccctcgtgcg ctctcctgtt ccgaccctgc cgcttaccgg atacctgtcc    1080
gcctttctcc cttcgggaag cgtggcgctt tctcatagct cacgctgtag gtatctcagt    1140
tcggtgtagg tcgttcgctc caagctgggc tgtgtgcacg aacccccgt tcagcccgac     1200 cgctgcgcct tatccggtaa ctatcgtctt gagtccaacc cggtaagaca cgacttatcg    1260
ccactggcag cagccactgg taacaggatt agcagagcga ggtatgtagg cggtgctaca    1320
gagttcttga agtggtggcc taactacggg tacactagaa gaacagtatt tggtatctgc    1380
gctctgctga agccagttac cttcggaaaa agagttggta gctcttgatc cggcaaacaa    1440
accaccgctg gtagcggtgg ttttttttgtt tgcaagcagc agattacgcg cagaaaaaaa    1500
ggatctcaag aagatccttt gatcttttct acggggtctg acgctcagtg gaacgaaaac    1560
tcacgttaag ggattttggt catgagatta tcaaaaagga tcttcaccta gatcctttta    1620
aattaaaaat gaagttttaa atcaatctaa agtatatatg agtaaacttg gtctgacagt    1680
taccaatgct taatcagtga ggcacctatc tcagcgatct gtctatttcg ttcatccata    1740
gttgcctgac tccccgtcgt gtagataact acgatacggg agggcttacc atctggcccc    1800
agtgctgcaa tgataccgcg agacccacgc tcaccggctc cagatttatc agcaataaac    1860
cagccagccg gaagggccga gcgcagaagt ggtcctgcaa ctttatccgc ctccatccag    1920
tctattaatt gttgccggga agctagagta agtagttcgc cagttaatag tttgcgcaac    1980
gttgttgcca ttgctacagg catcgtggtg tcacgctcgt cgtttggtat ggcttcattc    2040
agctccggtt cccaacgatc aaggcgagtt acatgatccc ccatgttgtg caaaaaagcg    2100
gttagctcct tcggtcctcc gatcgttgtc agaagtaagt tggccgcagt gttatcactc    2160
atggttatgg cagcactgca taattctctt actgtcatgc catccgtaag atgcttttct    2220
gtgactggtg agtactcaac caagtcattc tgagaatagt gtatgcggcg accgagttgc    2280
tcttgcccgg cgtcaatacg ggataatacc gcgccacata gcagaacttt aaaagtgctc    2340
atcattggaa aacgttcttc ggggcgaaaa ctctcaagga tcttaccgct gttgagatcc    2400
agttcgatgt aacccactcg tgcacccaac tgatcttcag catctttac tttcaccagc     2460 gtttctgggt gagcaaaaac aggaaggcaa aatgccgcaa aaaagggaat aagggcgaca    2520
cggaaatgtt gaatactcat actcttcctt tttcaatgat ctattacatt atgggtggta    2580
tgttggaata aaaatcaact atcatctact aactagtatt tacgttacta gtatattatc    2640
atatacggtg ttagaagatg acgcaaatga tgagaaatag tcatctaaat tagtggaagc    2700
tgaaacgcaa ggattgataa tgtaatagga tcaatgaata ttaacatata aaatgatgat    2760
aataatattt atagaattgt gtagaattgc agattccctt ttatggattc ctaaatcctc    2820
gactacgtcg ttaaggccgt ttctgacaga gtaaaattct tgagggaact ttcaccatta    2880
tgggaaatgg ttcaagaagg tattgactta aactccatca aatggtcagg tcattgagtg    2940
ttttttattt gttgtatttt ttttttttta gagaaaatcc tccaatatat aaattaggaa    3000
tcatagtttc atgattttct gttacaccta actttttgtg tggtgccctc ctccttgtca    3060
atattaatgt taaagtgcaa ttcttttttcc ttatcacgtt gagccattag tatcaatttg    3120
cttacctgta ttcctttaca tcctcctttt tctccttctt gataaatgta tgtagattgc    3180
gtatatagtt tcgtctaccc tatgaacata ttccattttg taatttcgtg tcgtttctat    3240
tatgaatttc atttataaag tttatgtaca aatatcataa aaaagagaa tctttttaag    3300
```

```
caaggatttt cttaacttct tcggcgacag catcaccgac ttcggtggta ctgttggaac   3360
cacctaaatc accagttctg atacctgcat ccaaaacctt tttaactgca tcttcaatgg   3420
ccttaccttc ttcaggcaag ttcaatgaca atttcaacat cattgcagca gacaagatag   3480
tggcgatagg gttgacctta ttctttggca aatctggagc agaaccgtgg catggttcgt   3540
acaaaccaaa tgcggtgttc ttgtctggca agaggccaa ggacgcagat ggcaacaaac   3600
ccaaggaacc tgggataacg gaggcttcat cggagatgat atcaccaaac atgttgctgg   3660
tgattataat accatttagg tgggttgggt tcttaactag gatcatggcg gcagaatcaa   3720
tcaattgatg ttgaaccttc aatgtaggga attcgttctt gatggtttcc tccacagttt   3780
ttctccataa tcttgaagag gccaaaacat tagctttatc caaggaccaa ataggcaatg   3840
gtggctcatg ttgtagggcc atgaaagcgg ccattcttgt gattctttgc acttctggaa   3900
cggtgtattg ttcactatcc caagcgacac catcaccatc gtcttccttt ctcttaccaa   3960
agtaaatacc tcccactaat tctctgacaa caacgaagtc agtacctta gcaaattgtg   4020 gcttgattgg agataagtct aaaagagagt cggatgcaaa gttacatggt cttaagttgg   4080
cgtacaattg aagttcttta cggattttta gtaaaccttg ttcaggtcta acactaccgg   4140
taccccattt aggaccaccc acagcaccta acaaaacggc atcagccttc ttggaggctt   4200
ccagcgcctc atctggaagt ggaacacctg tagcatcgat agcagcacca ccaattaaat   4260
gattttcgaa atcgaacttg acattggaac gaacatcaga aatagcttta agaaccttaa   4320
tggcttcggc tgtgatttct tgaccaacgt ggtcacctgg caaaacgacg atcttcttag   4380
gggcagacat tagaatggta tatccttgaa atatatatat atattgctga aatgtaaaag   4440
gtaagaaaag ttagaaagta agacgattgc taaccaccta ttggaaaaaa caataggtcc   4500
ttaaataata ttgtcaactt caagtattgt gatgcaagca tttagtcatg aacgcttctc   4560
tattctatat gaaaagccgg ttccggcgct ctcacctttc cttttctcc caattttca   4620 gttgaaaaag gtatatgcgt caggcgacct ctgaaattaa caaaaaattt ccagtcatcg   4680
aatttgattc tgtgcgatag cgcccctgtg tgttctcgtt atgttgagga aaaaaataat   4740
ggttgctaag agattcgaac tcttgcatct tacgatacct gagtattccc acagttaacg   4800
aagcatctgt gcttcatttt gtagaacaaa atgcaacgc gagagcgcta atttttcaaa   4860
caaagaatct agctgcattt ttacagaaca gaaatgcaac gcgagagcgc tatttacca   4920 acaaagaatc tatacttctt ttttgttcta caaaaatgca tcccgagagc gctatttttc   4980
taacaaagca tcttagatta ctttttttct ccttttgtgcg ctctataatg cagtctcttg   5040
ataacttttt gcactgtagg tccgttaagg ttagaagaag gctactttgg tgtctatttt   5100
ctcttccata aaaaagcct gactccactt cccgcgttta ctgattacta gcgaagctgc   5160
gggtgcattt tttcaagata aaggcatccc cgattatatt ctataccgat gtggattgcg   5220
catactttgt gaacagaaag tgatagcgtt gatgattctt cattggtcag aaaattatga   5280
acggtttctt ctattttgtc tctatatact acgtatagga aatgtttaca ttttcgtatt   5340
gttttcgatt cactctatga atagttctta ctacaatttt tttgtctaaa gagtaatact   5400
agagataaac ataaaaaatg tagaggtcga gtttagatgc aagttcaagg agcgaaaggt   5460
ggatgggtag gttatatagg gatatagcac agagatatat agcaaagaga tacttttgag   5520
caatgtttgt ggaagcggta ttcgcaatat tttagtagct cgttacagtc cggtgcgttt   5580
ttggtttttt gaaagtgcgt cttcagagcg cttttggttt tcaaaagcgc tctgaagttc   5640
ctatactttc tagagaatag gaacttcgga ataggaactt caaagcgttt ccgaaaacga   5700
```

-continued

```
gcgcttccga aaatgcaacg cgagctgcgc acatacagct cactgttcac gtcgcaccta    5760
tatctgcgtg ttgcctgtat atatatatac atgagaagaa cggcatagtg cgtgtttatg    5820
cttaaatgcg tacttatatg cgtctattta tgtaggatga aaggtagtct agtacctcct    5880
gtgatattat cccattccat gcggggtatc gtatgcttcc ttcagcacta ccctttagct    5940
gttctatatg ctgccactcc tcaattggat tagtctcatc cttcaatgct atcatttcct    6000
ttgatattgg atcatatgca tagtaccgag aaactagtgc gaagtagtga tcaggtattg    6060
ctgttatctg atgagtatac gttgtcctgg ccacggcaga agcacgctta tcgctccaat    6120
ttcccacaac attagtcaac tccgttaggc ccttcattga agaaatgag  gtcatcaaat    6180 gtcttccaat gtgagatttt gggccatttt ttatagcaaa gattgaataa ggcgcatttt    6240
tcttcaaagc tagctttaat gcggtagttt atcacagtta aattgctaac gcagtcaggc    6300
accgtgtatg aaatctaaca atgcgctcat cgtcatcctc ggcaccgtca ccctggatgc    6360
tgtaggcata ggcttggtta tgccggtact gccgggcctc ttgcgggata tcgtccattc    6420
cgacagcatc gccagtcact atggcgtgct gctagcgcta tatgcgttga tgcaatttct    6480
atgcgcaccc gttctcggag cactgtccga ccgctttggc cgccgcccag tcctgctcgc    6540
ttcgctactt ggagccacta tcgactacgc gatcatggcg accacacccg tcctgtggat    6600
gatccgggat cgaagaaatg atggtaaatg aaataggaaa tcaaggagca tgaaggcaaa    6660
agacaaatat aagggtcgaa cgaaaaataa agtgaaaagt gttgatatga tgtatttggc    6720
tttgcggcgc cgaaaaaacg agtttacgca attgcacaat catgctgact ctgtggcgga    6780
cccgcgctct tgccggcccg gcgataacgc tgggcgtgag gctgtgcccg gcggagtttt    6840
ttgcgcctgc atttttccaag gtttaccctg cgctaagggg cgagattgga gaagcaataa    6900
gaatgccggt tggggttgcg atgatgacga ccacgacaac tggtgtcatt atttaagttg    6960
ccgaaagaac ctgagtgcat ttgcaacatg agtatactag aagaatgagc caagacttgc    7020
gagacgcgag tttgccggtg gtgcgaacaa tagagcgacc atgaccttga aggtgagacg    7080
cgcataaccg ctagagtact ttgaagagga acagcaata  gggttgctac cagtataaat    7140
agacaggtac atacaacact ggaaatggtt gtctgtttga gtacgctttc aattcatttg    7200
ggtgtgcact ttattatgtt acaatatgga agggaacttt acacttctcc tatgcacata    7260
tattaattaa agtccaatgc tagtagagaa gggggtaac  accctccgc  gctcttttcc    7320 gattttttc  taaccgtgg  aatatttcgg atatcctttt gttgttccg  ggtgtacaat    7380 atggacttcc tcttttctgg caaccaaacc catacatcgg gattcctata ataccttcgt    7440
tggtctccct aacatgtagg tggcggaggg gagatataca atagaacaga taccagacaa    7500
gacataatgg gctaaacaag actacaccaa ttacactgcc tcattgatgg tggtacataa    7560
cgaactaata ctgtagccct agacttgata gccatcatca tatcgaagtt tcactaccct    7620
ttttccattt gccatctatt gaagtaataa taggcgcatg caacttcttt tctttttttt    7680
ttcttttctc tctccccgt  tgttgtctca ccatatccgc aatgacaaaa aaatgatgga    7740
agacactaaa ggaaaaaatt aacgacaaag acagcaccaa cagatgtcgt tgttccagag    7800
ctgatgaggg gtatctcgaa gcacgcgaaa cttttttcctt ccttcattca cgcacactac    7860
tctctaatga gcaacggtat acggccttcc ttccagttac ttgaatttga ataaaaaaaa    7920
agtttgctgt cttgctatca agtataaata gacctgcaat tattaatctt ttgtttcctc    7980
gtcattgttc tcgttccctt t                                              8001
```

<210> SEQ ID NO 30
<211> LENGTH: 5857
<212> TYPE: DNA
<213> ORGANISM: Homo sapiens

<400> SEQUENCE: 30

| | | | | | |
|---|---|---|---|---|---|
| ggccgcaaat | taaagccttc | gagcgtccca | aaaccttctc | aagcaaggtt | ttcagtataa | 60 |
| tgttacatgc | gtacacgcgt | ctgtacagaa | aaaaagaaaa | aatttgaaat | ataaataacg | 120 |
| ttcttaatac | taacataact | ataaaaaaat | aaatagggac | ctagacttca | ggttgtctaa | 180 |
| ctccttcctt | ttcggttaga | gcggatgtgg | ggggagggcg | tgaatgtaag | cgtgacataa | 240 |
| ctaattacat | gatgcggccc | tctagatgca | tgctcgagcg | gccgccagtg | tgatggatat | 300 |
| ctgcagaatt | ccagcacact | ggcggccgtt | actagtggat | ccgagctcgg | taccaagctt | 360 |
| aatattccct | atagtgagtc | gtattacagc | tgctagtagt | ccgatccggg | ttttttctc | 420 |
| cttgacgtta | aagtatagag | gtatattaac | aatttttgt | tgatactttt | attacatttg | 480 |
| aataagaagt | aatacaaacc | gaaaatgttg | aaagtattag | ttaaagtggt | taatgcagtt | 540 |
| tttgcattta | tatatctgtt | aatagatcaa | aaatcatcgc | ttcgctgatt | aattacccca | 600 |
| gaaataaggc | taaaaaacta | atcgcattat | catcctatgg | ttgttaattt | gattcgttca | 660 |
| tttgaaggtt | tgtggggcca | ggttactgcc | aattttcct | cttcataacc | ataaaagcta | 720 |
| gtattgtaga | atctttattg | ttcggagcag | tgcggcgcga | ggcacatctg | cgtttcagga | 780 |
| acgcgaccgg | tgaggacgag | gacgcacgga | ggagagtctt | ccttcggagg | gctgtcaccc | 840 |
| gctcggcggc | ttctaatccg | tactagtgga | tcatccccac | gcgccctgta | gcgcccatt | 900 |
| aagcgcggcg | ggtgtggtgg | ttacgcccag | cgtgaccct | acacttccca | ccgccctagc | 960 |
| ccccgctcct | ttcgctttct | tcccttcctt | tctcgccacg | ttcgccggct | ttccccgtca | 1020 |
| agctctaaat | cggggcatcc | gtttaccctt | ccgatttact | gctttacggc | acctcgaccc | 1080 |
| caaaaaactt | gattagggtg | atggttcacg | tagtgggcca | tcgccctgat | agacccttt | 1140 |
| tcgccctttg | acgttggagt | ccacgttctt | taatagtgga | ctcttgttgg | aaactggaac | 1200 |
| aacactcaac | cctatctcgg | tctattcttt | tgatttataa | gggattttgc | cgatttcggg | 1260 |
| ctattcgtta | aaaaatgagc | tgatttaaca | aaaatttaac | gcgaatttta | acaaaatatt | 1320 |
| aacgtttaca | atttaaatat | ttgcttatac | aatcttcctg | tttttggggc | ttttctgatt | 1380 |
| atcaaccggg | gtggagcttc | ccattgcgaa | taccgcttcc | acaaacattg | ctcaaaagta | 1440 |
| tctctttgct | atatatctct | gtgctatatc | cctatataac | ctacccatcc | acctttcgct | 1500 |
| ccttgaactt | gcatctaaac | tcgacctcta | catttttat | gtttatctct | agtattactc | 1560 |
| tttagacaaa | aaaattgtag | taagaactat | tcatagagtg | aatcgaaaac | aatacgaaaa | 1620 |
| tgtaaacatt | tcctatacgt | agtatataga | gacaaaatag | aagaaaccgt | tcataatttt | 1680 |
| ctgaccaatg | aagaatcatc | aacgctatca | ctttctgttc | acaaagtatg | cgcaatccac | 1740 |
| atcggtatag | aatataatcg | gggatgcctt | tatcttgaaa | aaatgcaccc | gcagcttcgc | 1800 |
| tagtaatcag | taaacgcggg | aagtggagtc | aggcttttt | tatggaagag | aaaatagaca | 1860 |
| ccaaagtagc | cttcttctaa | ccttaacgga | cctacagtgc | aaaaagttat | caagagactg | 1920 |
| cattatagag | cgcacaaagg | agaaaaaaag | taatctaaga | tgctttgtta | gaaaaatagc | 1980 |
| gctctcggga | tgcattttg | tagaacaaaa | agaagtata | gattctttgt | tggtaaaata | 2040 |
| gcgctctcgc | gttgcatttc | tgttctgtaa | aaatgcagct | cagattcttt | gtttgaaaaa | 2100 |
| ttagcgctct | cgtcgcgttg | catttttgtt | ttacaaaaat | gaagcacaga | ttcttcgttg | 2160 |

```
gtaaaatagc gctttcgcgt tgcatttctg ttctgtaaaa atgcagctca gattctttgt     2220
ttgaaaaatt agcgctctcg cgttgcattt ttgttctaca aaatgaagca cagatgcttc     2280
gttaacaaag atatgctatt gaagtgcaag atggaaacgc agaaaatgaa ccggggatgc     2340
gacgtgcaag attacctatg caatagatgc aatagtttct ccaggaaccg aaatacatac     2400
attgtcttcc gtaaagcgct agactatata ttattataca ggttcaaata tactatctgt     2460
ttcagggaaa actcccaggt tcggatgttc aaaattcaat gatgggtaac aagtacgatc     2520
gtaaatctgt aaaacagttt gtcggatatt aggctgtatc tcctcaaagc gtattcgaat     2580
atcattgaga agctgcagcg tcacatcgga taataatgat ggcagccatt gtagaagtgc     2640
cttttgcatt tctagtctct ttctcggtct agctagtttt actacatcgc gaagatagaa     2700
tcttagatca cactgccttt gctgagctgg atcaatagag taacaaaaga gtggtaaggc     2760
ctcgttaaag gacaaggacc tgagcggaag tgtatcgtac agtagacgga gtatctagta     2820
tagtctatag tccgtggaat taattctcat cttttgacagc ttatcatcga taagctagct     2880
tttcaattca attcatcatt tttttttat tcttttttt gatttcggtt tctttgaaat     2940 tttttgatt cggtaatctc cgaacagaag gaagaacgaa ggaaggagca cagacttaga     3000
ttggtatata tacgcatatg tagtgttgaa gaaacatgaa attgcccagt attcttaacc     3060
caactgcaca gaacaaaaac ctgcaggaaa cgaagataaa tcatgtcgaa agctacatat     3120
aaggaacgtg ctgctactca tcctagtcct gttgctgcca agctatttaa tatcatgcac     3180
gaaaagcaaa caaacttgtg tgcttcattg gatgttcgta ccaccaagga attactggag     3240
ttagttgaag cattaggtcc caaaatttgt ttactaaaaa cacatgtgga tatcttgact     3300
gatttttcca tggagggcac agttaagccg ctaaaggcat tatccgccaa gtacaatttt     3360
ttactcttcg aagacagaaa atttgctgac attggtaata cagtcaaatt gcagtactct     3420
gcgggtgtat acagaatagc agaatgggca gacattacga atgcacacgg tgtggtgggc     3480
ccaggtattg ttagcggttt gaagcaggcg gcagaagaag taacaaagga acctagaggc     3540
cttttgatgt tagcagaatt gtcatgcaag ggctccctat ctactggaga atatactaag     3600
ggtactgttg acattgcgaa gagcgacaaa gattttgtta tcggctttat tgctcaaaga     3660
gacatgggtg gaagagatga aggttacgat tggttgatta tgacacccgg tgtgggttta     3720
gatgacaagg gagacgcatt gggtcaacag tatagaaccg tggatgatgt ggtctctaca     3780
ggatctgaca ttattattgt tggaagagga ctatttgcaa agggaaggga tgctaaggta     3840
gagggtgaac gttacagaaa agcaggctgg gaagcatatt tgagaagatg cggccagcaa     3900
aactaaaaaa ctgtattata agtaaatgca tgtatactaa actcacaaat tagagcttca     3960
atttaattat atcagttatt acccattgaa aaaggaagag tatgagtatt caacatttcc     4020
gtgtcgccct tattccctttt tttgcggcat tttgccttcc tgttttgct cacccagaaa     4080 cgctggtgaa agtaaaagat gctgaagatc agttgggtgc acgagtgggt tacatcgaac     4140
tggatctcaa cagcggtaag atccttgaga gttttcgccc cgaagaacgt tttccaatga     4200
tgagcacttt taaagttctg ctatgtgata cactattatc ccgtattgac gccgggcaag     4260
agcaactcgg tcgccgcata cactattctc agaatgactt ggttgagtac tcaccagtca     4320
cagaaaagca tcttacggat ggcatgacag taagagaatt atgcagtgct gccataacca     4380
tgagtgataa cactgcggcc aacttacttc tgacaacgat cggaggaccg aaggagctaa     4440 ccgcttttttt gcacaacatg ggggatcatg taactcgcct tgatcgttgg gaaccggagc     4500
```

-continued

```
tgaatgaagc cataccaaac gacgagagtg acaccacgat gcctgtagca atgccaacaa  4560
cgttgcgcaa actattaact ggcgaactac ttactctagc ttcccggcaa caattaatag  4620
actgaatgga ggcggataaa gttgcaggac cacttctgcg ctcggccctt ccggctggct  4680
ggtttattgc tgataaatct ggagccggtg agcgtgggtc tcgcggtatc attgcagcac  4740
tggggccaga tggtaagcgc tcccgtatcg tagttatcta cacgacgggg agtcaggcaa  4800
ctatggatga acgaaataga cagatcgctg agataggtgc ctcactgatt aagcattggt  4860
aactgtcaga ccaagtttac tcatatatac tttagattga tttaaaactt catttttaat  4920
ttaaaaggat ctaggtgaag atcctttttg ataatctcat gaccaaaatc ccttaacgtg  4980
agttttcgtt ccactgagcg tcagaccccg tagaaaagat caaaggatct tcttgagatc  5040
ctttttttct gcgcgtaatc tgctgcttgc aaacaaaaaa accaccgcta ccagcggtgg  5100
tttgtttgcc ggatcaagag ctaccaactc tttttccgaa ggtaactggc ttcagcagag  5160
cgcagatacc aaatactgtc cttctagtgt agccgtagtt aggccaccac ttcaagaact  5220
ctgtagcacc gcctacatac ctcgctctgc taatcctgtt accagtggct gctgccagtg  5280
gcgataagtc gtgtcttacc gggttggact caagacgata gttaccggat aaggcgcagc  5340
ggtcgggctg aacggggggt tcgtgcacac agcccagctt ggagcgaacg acctacaccg  5400
aactgagata cctacagcgt gagctatgag aaagcgccac gcttcccgaa gggagaaagg  5460
cggacaggta tccggtaagc ggcagggtcg gaacaggaga gcgcacgagg gagcttccag  5520
ggggaaacgc ctggtatctt tatagtcctg tcgggtttcg ccacctctga cttgagcgtc  5580
gatttttgtg atgctcgtca ggggggcgga gcctatggaa aaacgccagc aacgcggcct  5640
ttttacggtt cctgggcttt tgctggcctt ttgctcacat gttctttcct gcgttatccc  5700
ctgattctgt ggataaccgt attaccgcct ttgagtgagc tgataccgct cgccgcagcc  5760
gaacgaccga gcgcagcgag tcagtgagcg aggaagcgga agagcgccca atacgcaaac  5820
cgcctctccc cgcgcgttgg ccgattcatt aatgcag                           5857
```

```
<210> SEQ ID NO 31
<211> LENGTH: 18
<212> TYPE: DNA
<213> ORGANISM: Homo sapiens

<400> SEQUENCE: 31
aagcttcccg ggaccatg                                                  18
```

METHOD FOR DETECTING PROTEIN-PROTEIN INTERACTIONS AND A KIT THEREFOR

FIELD OF THE INVENTION

The present invention relates generally to molecular biology and more specifically to a method for identifying protein pairs involved in protein—protein interactions.

BACKGROUND OF THE INVENTION

The phrase "protein—protein interaction" refers to the ability of two protein molecules to bind to each other so as to form a complex. Such protein—protein interactions are involved in a large variety of biological processes including, for example, signal transduction pathways, enzyme-substrate interactions, viral adhesions and the formation of antibody-antigen complexes.

Many proteins are capable of interacting with a number of other proteins. Identifying and characterizing such interactions are highly important in understanding biological mechanisms, signal transduction pathways, etc. in characterizing the molecular basis of various diseases as disorders and in the is design of therapies.

A defect in a protein preventing it from participating in a protein—protein interaction can. as may be appreciated, have deleterious effects on a cell.

The ability to identify and characterize protein—protein interactions permits the identification of the defects in such interactions associated with a diseased state. The identification of such defects provides a target for potential therapies to cure or ameliorate the disease. In addition, the identification and characterization of protein—protein interactions provides a means to screen for drugs that alter the interaction. Such drugs can be useful, for example, to treat a disease caused, at least in part, by an aberrant protein—protein interaction.

Methods for assaying protein—protein interactions have been reviewed in Allen et al., *Trends Biochem. Sci.*, 20:511–516, 1995.

Proteins involved in a protein—protein interaction can be identified by detecting the presence of the protein complex in a cell or in a body fluid, and purifying the proteins forming the complex by biochemical methods. Such methods of isolation, however, are extremely tedious, particularly when the protein is expressed at low levels or if only a few cells express the protein. Immobilization of proteins on membrane filters has more recently lead to the development of filter based assays using proteins translated from cDNA molecules obtained, for example, from phage. However, the filter based assays, while being more sensitive, are also often very tedious.

A genetic method of identifying protein—protein interactions has also been developed (Fields et al, *Nature*, 340:245–246, 1989). In this method, known as the "two hybrid assay", one protein is fused to a DNA binding domain (typically from the Gal4 protein) while another protein is fused to a strong transcription activation domain. Binding of the two proteins inside a cell thus generates a functional transcription factor that is detected by a change in phenotype of the cell due to the expression of genes whose transcription is under the control of Gal4 DNA elements. The two hybrid system however, suffers from several limitations. First, protein pairs in which one of the proteins possesses transcriptional activity on its own, obviously cannot be analyzed. This includes bona fide transcription factors as well as proteins containing domains that fortuitously interact with the transcription machinery. Another limitation of the two hybrid system results from the toxicity of many proteins, for example certain homeodomain proteins and cell cycle regulators, when expressed in the nucleus. Furthermore, the two hybrid system produces false positive or false negative results when one of the proteins undergoes a conformational chance in the nucleus.

Another genetic method, the "Sos Recruitment System" (SRS) has also been described (Aronheim, A., *Mol Cell. Biol.*, 17:3094–3102, 1997). This method is based on the observation that localization of the protein hSos (the Ras guanyl nucleotide exchange factor) at the plasma membrane is essential for activating the Ras pathway and is therefore essential for viability. A yeast strain, such as cdc25-2, containing a temperature sensitive allele of Cdc25, (a yeast homologue of hSos) is thus viable only at the permissive temperature (24° C.). In the SRS system, a first protein (the bait protein) is fused to hSos while a second protein (the prey protein) is fused to a membrane localization domain. A protein—protein interaction between the bait and prey proteins localizes hSos at the plasma membrane. This complements the Cdc25 mutation which is detected as cell growth at the restrictive temperature (36° C.). However, the SRS also exhibits several limitations. First, about 20–30% of all bait proteins fused to hSos result in prey-independent complementation of Cdc25, a fact which yields a relatively high unspecific background signal ("noise"). Another limitation of the SRS system is that the effector part of the hSos is relatively large (150 Kda). This tends to complicate the fusion to hSos of both large bait proteins as well as short bait proteins.

Another problem of the SRS system is due to the fact that Ras encoded proteins are able to bypass the Cdc25 mutation because the yeast GTPase activating proteins (IRA genes) hydrolyze GTP bound to mammalian Ras proteins rather inefficiently thus leaving the Ras proteins in their active GTP-bound form.

SUMMARY OF THE INVENTION

The present invention makes use of the fact that in order for it to function. Ras needs to be localized at the plasma membrane. This localization normally occurs via the covalent attachment of a lipid moiety to cysteine 186 that anchors Ras at the membrane. Ras contains a consensus CAAX box located at the C-terminal end which undergoes farnesylation and subsequently palmitoylation. A Ras lacking the farnesylation box (CAAX) is non-functional since it cannot be localized at the membrane. The present invention thus makes use of cells with a Ras that is mutated such that it cannot be localized at the membrane, e.g. lacking the farnesylation box or having a mutation therein. These cells are "engineered" such that they express two fusion proteins, one fusion protein comprising a first protein (referred to herein at times as the "bait") and a Ras protein which is mutated such that it cannot bind to the plasma membrane, and another fusion protein which comprises a second protein (referred to herein at times as the "prey") and a membrane localization domain. If the bait binds the prey then the Ras fused to the prey becomes localized at the membrane and can thereby function.

FIG. 1 shows a schematic representation of the invention. In panel A, a cell incapable of expressing a functional Ras is made to express a Ras that cannot be localized at the membrane (and is thus non-functional) fused to a bait protein. A putative prey protein has been localized at the plasma membrane. A protein—protein interaction between the prey and bait proteins (panel B) localizes Ras at the plasma membrane. This produces a functional Ras that is detected as a phenotypic change in the cell.

This Ras Recruiting System (RRS) has several advantages over the SRS system:

1. The Ras protein is relatively small, thereby overcoming several of the technical limitations and practical problems posed by the large size of Sos as described above.
2. The RRS system exhibits substantially less false positive results, as compared to the SRS, with mammalian cDNA expression library screens and therefore represents a more efficient system for characterizing interacting proteins.

The invention thus provides a method for identifying a protein—protein interaction between a first protein and a second protein comprising the steps of:

(a) expressing in a cell which is incapable of activating a Ras protein;
  (aa) a first nucleic acid sequence encoding a first fusion protein, said first fusion protein comprising a Ras protein mutated such that it cannot localize at the cell membrane and does not require an exchange factor fused to said first protein; and
  (ab) a second nucleic acid sequence encoding a second fusion protein said second fusion protein, comprising said second protein fused to a plasma membrane localization domain; and
(b) determining whether there is a phenotypic expression of a functional Ras protein in said cell, the presence of a functional Ras protein in said cell indicating a protein—protein interaction between said first protein and said second protein.

In a preferred embodiment of the invention, the mutated Ras protein, which forms part of the fusion proteins encoded by the first nucleic acid sequence, lacks a farnesylation box.

In another preferred embodiment of the invention, the cell incapable of expressing a functional Ras is of the yeast strain cdc 25-2. The Ras of this cell is non-functional at the restrictive temperature (36° C.) due to a lack of a functional guanyl nucleotide exchange factor. Production of a functional Ras in these cells by an interaction between a bait protein and a prey protein according to the invention is detected as growth independent of a functional exchange factor at such a restrictive temperature, e.g. at about 33–37° C., typically at about 36° C.

The method of the invention is useful for screening of gene libraries to fixed expression products that interact with a specific protein. As already pointed out above determining protein—protein interaction may be highly important for drug development. In addition, determining such interaction may serve as a diagnostic trend; for example, a specific pattern of interaction of one protein with others, may serve as an indication of a normal or a mutated protein.

The method of the invention lends itself also to application in high throughput screening techniques. Cells may be automatically supplemented with DNA constructs, e.g. plasmids, under conditions in which such constructs will be internalized by the cells and then screened automatically for such with a Ras phenotype expression.

The invention also provides a system for use in determining whether a first protein is capable of binding to a second protein, comprising:

(a) a culture of cells incapable of activating a Ras protein;
(b) a first nucleic acid vector, for inserting therein a DNA sequence encoding a first fusion protein which comprises a Ras protein mutated such that it cannot localize to the cell membrane and does not require an exchange factor and said first protein;
(c) a second nucleic acid vector, which may be the same or different than said first nucleic acid vector, for inserting therein a DNA sequence encoding a second fusion protein which comprises said second protein and a plasma membrane localization domain;
(d) reagents and devices for transfecting the cells with said first and said second nucleic acid;
(e) a monitoring arrangement for monitoring phenotypic Ras expression in said cells.

Also provided by the invention is a kit comprising some or all of the constituents of the above system.

Localization of a mammalian Ras fused to a bait of interest at the plasma membrane through a protein—protein interaction in a temperature sensitive mutant such as cdc25-2 permits growth at 36° C. Ras localization can also complement a temperature sensitive mutant yeast strain that is defective in its exchange factor. hSos, however, complements the yeast cdc25 mutant strain only when expressed in the membrane, but $Ras^{ts}$ fails to do so in the yeast $Ras^{ts}$ mutant strain, which is defective in its Ras. This eliminates isolation of mammalian Ras exchange factors in a library screen.

As provided by the invention, mammalian expression vectors comprising regions encoding for interacting protein partners used in the yeast RRS system can be co-tansfected with a reporter gene such as a chloramphenicol acetyl transferase (CAT) or luciferase gene under the control of either AP-1 responsive elements or Ras responsive elements. Cultured mammalian cells expressing these plasmids allow a protein—protein interaction known to occur in yeast to be quantitatively detected in mammalian cells by monitoring the enzymatic activity of the reporter gene following the protein—protein interaction and recruitment of activated Ras to the plasma membrane. Use of reporter genes in mammalian cells allows direct evidence of a protein—protein interaction initially identified in yeast and improved assessment of drug effectiveness directly in mammalian cells.

The invention also provides a positive control for proteins for which a protein partner is not detected in a library screening as described above. In cells not expressing a functional Ras, a fusion protein is expressed comprising a functional Ras fused to two bait proteins. The first bait ("the tester bait") is the protein having no known protein partners while the second bait ("the control bait") is a protein having a known protein partner. The ability of the control bait moiety to bind its known prey is determined. A protein—protein reaction occurring between the control bait moiety and its prey demonstrates that the gene for the fusion moiety is expressed at adequate levels that the Ras moiety of the fusion protein is functional, and that the Ras pathway is intact. This would provide genetic evidence that screening with the tester bait is potentially possible and worthwhile.

The fusion of a tester bait and a control bait to a single Ras molecule may be used for mapping the amino acids involved in an interaction between the tester bait and its prey. The tester bait is subjected to random mutagenesis and inserted fused in fame with the control bait. The tester bait DNA is inserted in frame with that of Ras and the control bait and expressed, for example, in cdc25-2 cells of one mating type. The cells are then mated with cells of the opposite mating type expressing either the prey of the tester bait or the control bait. Cells able to grow with the control bait but not with the tester bait prey indicate the integration of a mutation that affects the tester bait prey binding that is not due to a frame shift or nonsense mutation.

Similarly this embodiment may also be used for screening drugs for the ability to inhibit an interaction between a tester bait and its prey while not inhibiting an interaction between the control bait and its prey.

BRIEF DESCRIPTION OF THE DRAWINGS

In order to understand the invention and to see how it may be carried out in practice, a preferred embodiment will now be described, by way of non-limiting examples only, with reference to the accompanying drawings, in which.

EXAMPLES

Material and Methods
Plasmids and Constructs

Ras plasmid construction: Ras-specific oligonucleotides were designed to generate a Ras fragment corresponding to amino acids 2–185. Ras DNA fragment was designed to contain 5'-AAG CTT CCC GGG ACC ATG (SEQ ID NO: 31) to provide HindIII SmaI NcoI restriction cites to allow N-terminal fusion and either 5'-TGG ATC CTC or 5'-GGA ATT CTC to provide either a BamHI or EcoRI restriction sites respectively to allow C-terminal fusion.

ADNS expression vectors: p110-RasΔF-Wt., p110-Ras(61)ΔF encode for p110β amino acids 31 to 150 fused to either wild type Ras or activated Ras(L61) respectively devoid of its CAAX box. JZ-RasΔF-Wt., JZ-Ras(61)ΔF encode for c-Jun DNA binding domain amino acids 249–331 fused to Ras as described above. Sos-C-Ras(61)ΔF encodes for hSoc C-terminal region amino acids 1066–1333 fused to activated Ras(L61) devoid of its CAAX box. PAK65, amino acids 3–215, was fused to Ras(61)ΔF. The DNA fragments of p110, JZ, Sos-C and PAK65 were fused to Ras(L61)ΔF into HindIII-SmaI. JDP2 cDNA was fused to Ras to its C-terminal domain using EcoRI-XhoI restriction and ligated by three fragments ligation into ADNS HindIII-SalI to generate ADNS-Ras(61)ΔF-JDP2.

Yes2 expression vectors: Yes-M, Yes-M-p85, Yes-M-Fos are as described, Yes-M-Grb2 and Yes-M*-Grb2 encode for full length Grb2 fused to either myristoylation (M) or myristoylated defective sequence. Yes-M-PLCγ2 corresponds to amino acids 405–1252 of PLCγ2 fused to Yes-M. Yes-M-p85(SH3) corresponds to amino acids 2–84 of p85. Yes-M-GAP(SH3) corresponds to amino acids 262–345 of mammalian GAP.

The different Rac1 plasmids were constructed into pYes2 expression plasmid (Invitrogene Inc.).

Yeast Growth and Manipulations

Conventional yeast transfection and manipulation protocols were used. Cells were plated on either glucose minimal medium containing the relevant amino acids, 2% glucose, 0.5% $NH_4SO_4$, 017% yeast extract and 4% agar or galactose glucose. YPD medium contains: 1% yeast extract, 2% bacto peptone, 2% glucose. Replica plating was performed with homemade disposable velvet replica plating.

Library Screening

Screening of the library was performed stepwise. First the bait was cotransfected into cdc25-2 cells together with Yes(trp)-mGAP expression plasmid. Transfonnants were selected on glucose minimal medium lacking the amino acids leucine and tryptophan at 24° C. Subsequently, 3 ml culture was grown in liquid at 24° C. overnight and used to inoculate 200 ml medium for an additional 12 hours. Cells were pelleted and resuspended in 200 ml YPD medium for 3–5 hours at 24° C. and used directly for transfection with 20–40 μg of library plasmid DNA. Cells were plated on about twenty 10 cm plates resulting in 5,000–10,000 transformants/plate.

Example 1

Use of RRS to Detect an Interaction Between Cytoplasmic Protein Pairs

Figure 1:
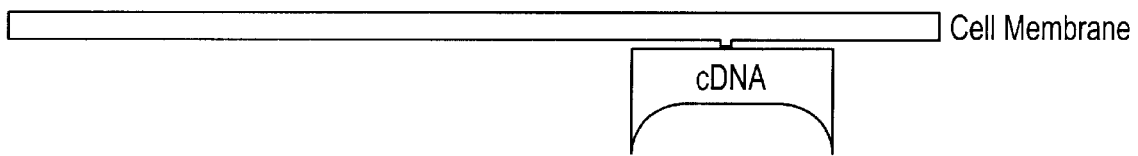
FIG. 1 shows a schematic diagram of the RRS system.
Figure 1:
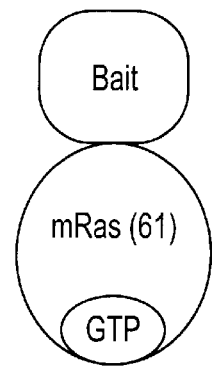
Figure 1:
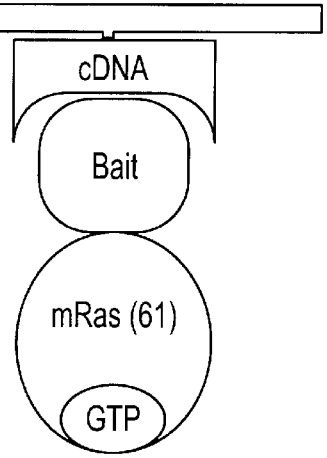
Figure 2:
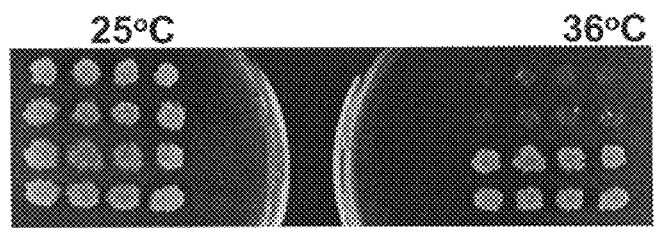
FIG. 2 shows the complementation of the cdc25-2 mutation through protein—protein interactions. A.-p110-p85 interaction. B.-Jun-Fos inter-action. C.-Grb2-hSos-C.
Figure 2:
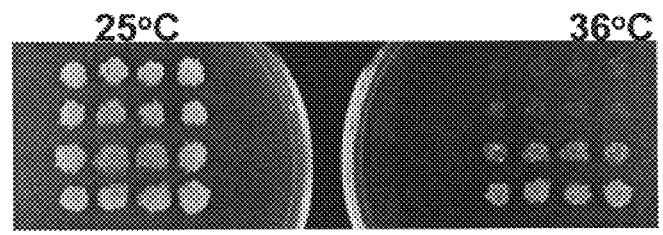
Figure 2:
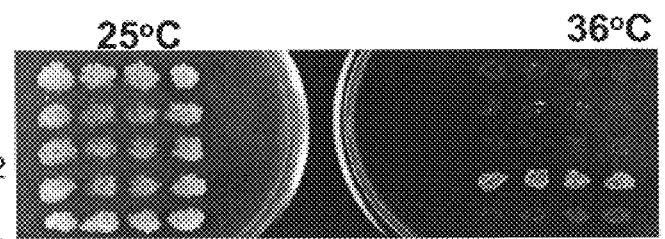

The interaction between two cytoplasmic proteins, the phosphatidyl-inositol-3-phosphate kinase subunits p110 and p85 was tested using the RRS system (FIG. 2A). The p85 interacting domain of p110 was fused to either activated or wild type mammalian cytoplasmic Ras p110-Ras(61)ΔF and p110RasβF-Wt., respectively. Plasmids were cotransfected in different combinations with either the Yes2 empty expression vector or a plasmid encoding for myristoylated p85 (Yes-M or Yes-M-p85 respectively) into Cdc25-2 yeast cells and grown at 24° C. on glucose minimal medium supplemented with the appropriate amino acids and bases. Four independent transformants were grown at 24° C. (left panel), replica plated onto appropriately supplemented galactose minimal plates and grown at 36° C. (right panel). Constructs used are described in Material and Methods. Only transformants expressing both the p110-Ras fusion protein and membrane anchored p85 were able to grow at 36° C. No significant difference was observed when p110 was fused to either the wild type or activated cytoplasmic Ras.

Example 2

Use of RRS to Detect an Interaction Between Nuclear Protein Pairs

The interaction of two nuclear proteins c-Jun and c-Fos was tested using the RRS (FIG. 2B). The DNA binding domain of c-Jun was fused to either activated or wild type mammalian cytoplasmic Ras (JZ-Ras(61)ΔF and JZ-RasΔF-Wt. respectively). These plasmids were cotransfected with their Yes2 empty expression vector or a plasmid encoding myristoylated c-Fos (Yes-M or Yes-M-Fos) to cdc25-2 yeast cells and grown at 24° C. (FIG. 2B, left panel). Transformants were isolated and tested for their ability to grow at the restrictive temperature 36° C. (FIG. 2B, right panel). Only transformants expressing both the c-Jun-Ras fusion protein and membrane anchored c-Fos were able to grow at the restrictive temperature.

Example 3

Use of RRS to Detect an Interaction Between hSos C-terminal Domain and Crb2

The interaction of the C-terminal region of hSos (containing the proline rich region) with the adapter protein Grb2 was tested (FIG. 2C). hSos C-terminal domain was fused to cytoplasmic activated mammalian Ras (Soc-C-Ras(61)ΔF). This plasmid was cotransfected with either empty vector (Yes-M), membrane anchored Grb2 (Yes-M-Grb2) or cytoplasmic Grb2 (Yes-M*-Grb2) to cdc25-2 yeast cells and grown at 24° C. on appropriate medium (FIG. 2C, left panel). Transformants were isolated and tested for their ability to grow at 36° C. Only transformants expressing both the Soc C-terminal fusion protein and membrane anchored Grb2 were able to grow at 36° C. (FIG. 2C, right panel). RRS is thus superior to the SRS system for identification of Soc C-terminal interacting proteins, since this domain confers an inhibitory activity on Sos function.

Example 4

Pak65

Figure 3:
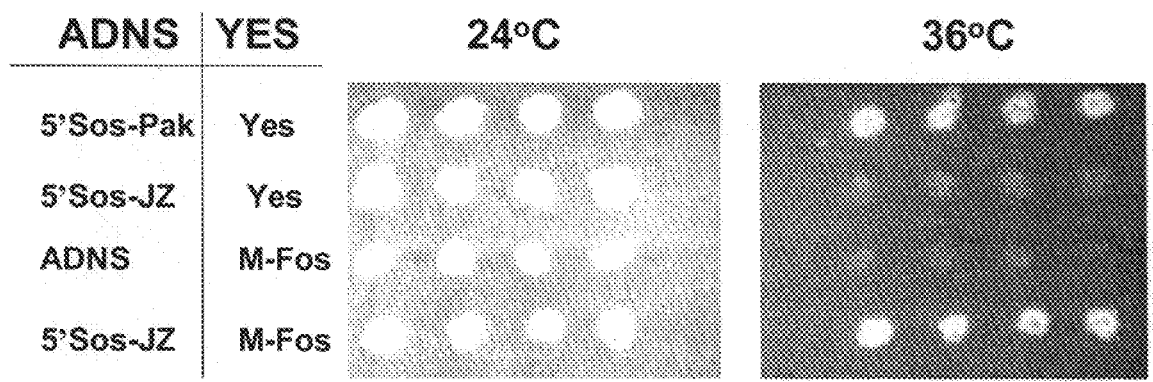
FIG. 3 shows the complementation of the cdc25-2 mutation by 5'Sos-Pak bait in a prey-independent manner.

As described above, one of the problems associated with the SRS system is prey independent-activity of hSos fused to some proteins. One such protein is the p21 Activated Kinase, Pak65. Pak 65 activates Rac and Cdc42 by binding them in a GTP dependent manner. Despite considerable efforts, little information is available concerning the role of Pak65 in signal transduction. The Pak65 regulatory domain contains two protein modules known to mediate protein— protein interactions: a proline rich region that binds SH3 containing proteins and a Cdc42/Rac interacting binding domain (CRIB) found in a number of proteins that bind the small GTPase proteins from the Rho family. In order to gain insight into Pak65 function, proteins binding to the Pak65 regulatory domain using the SRS system were screened (FIG. 3). The Pak65 regulatory domain was fused to 5'Sos and expressed in cdc25-2 yeast cells. Transformants expressing, 5'Sos-Pak exhibit efficient growth even in the absence of a protein partner (FIG. 3. This renders the SRS system ineffective for screening with the Pak65 bait.

Figure 4:
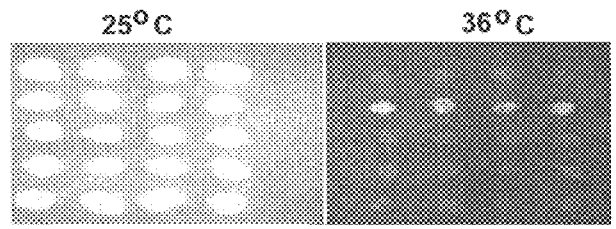
FIG. 4 shows the interaction of Pak65 regulatory domain (Pak) with known protein partners using the RRS system. A.-Pak65 interaction with different SH3 containing proteins; B.-Pak65 interaction with Rac1 mutants.
Figure 4:
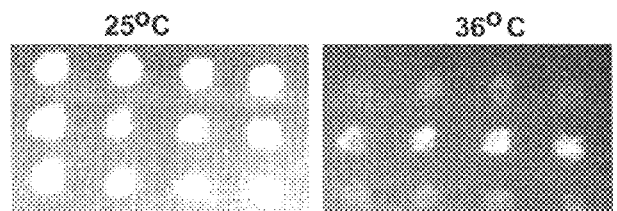

However, cdc25-2 yeast transformants expressing, the Pak65 regulatory domain fused to the cytoplasmic activated Ras (Pak-Ras(61)ΔF were unable to grow at the 36° C. (FIG. 4A, right panel) and therefore the Pak65 bait could be used for further analysis.

Example 5

Use of RRS for Isolation of Novel Protein Interactions

Figure 5:
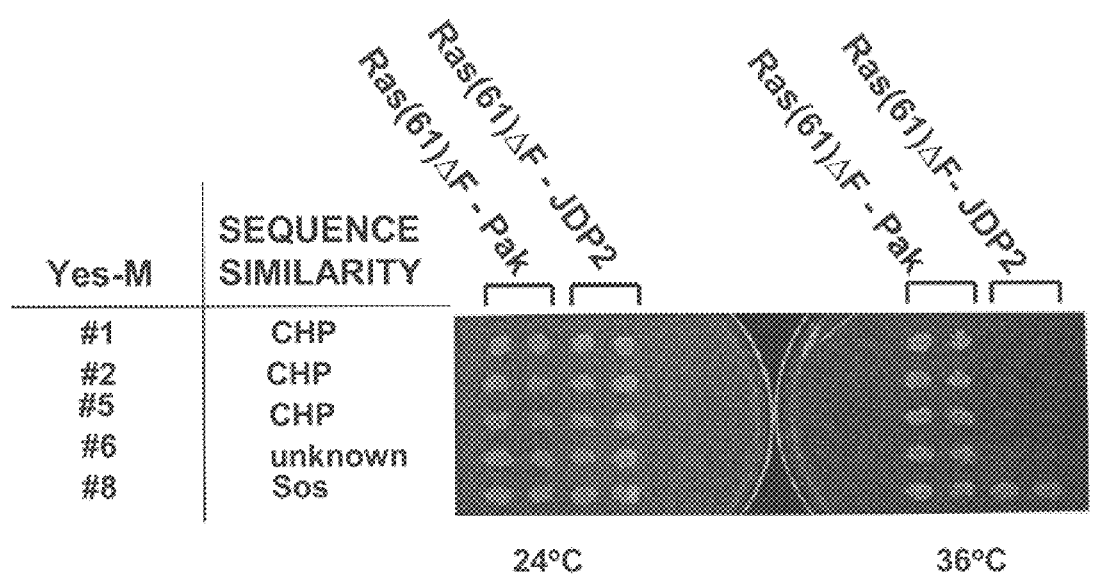
FIG. 5 shows the isolation of novel protein interaction using Pak65 regulatory domain as a bait and the RRS system.

The Pak65 regulatory domain was used as a bait to screen a rat pituitary cDNA expression library fused to a membrane localization sequence. Expression of the library cDNA insert plasmid is under the control of the GAL1 promoter. About 500,000 independent transformants were screened for interaction with Pak-Ras(61)ΔF bait in the presence of a plasmid encoding for mammalian GAP. Five clones were isolated that exhibited efficient cell growth at 36° C. only when grown under galactose inducing conditions. Plasmids derived from these yeast clones were cotransfected with either the original Pak65 bait (Pk-Ras(61)ΔF) or an irrelevant bait (Ras(61)ΔF-JDP2). DNA plasmids from four independent clones encoded proteins that exhibited a specific interaction with Pak65 bait resulting in efficient growth at 36° C. but did not grow when expressed with the irrelevant bait at 36° C. (FIG. 5). Only one plasmid DNA produced efficient growth at 36° C. with both the specific and non-specific baits. Sequence analysis of this clone identified it as a Sos-homologue which would be expected to activate yeast Ras and bypass the requirement for mammalian Ras translocation.

What is claimed is:

1. A method for identifying a protein—protein interaction between a first protein and a second protein comprising the steps of:
 (a) expressing in a cell which is incapable of activating a Ras protein;
  (aa) a first nucleic acid sequence encoding a first fusion protein, said first fusion protein comprising a Ras protein mutated such that it cannot localize at the cell membrane and does not require an exchange factor fused to said first protein; and
  (ab) a second nucleic acid sequence encoding a second fusion protein said second fusion protein comprising said second protein fused to a plasma membrane localization domain; and
 (b) determining whether there is a phenotypic expression of a functional Ras protein in said cells the presence of a functional Ras protein in said cell indicating a protein—protein interaction between said first protein and said second protein.

2. The method of claim 1, wherein the mutated Ras protein comprised in the fusion protein encoded by said first nucleic acid sequence, lacks a farnesylation box.

3. The method of claim 1, wherein said cell is a yeast cell.

4. The method of claim 3, wherein said yeast cell is a *Saccharomyces cerevesiae* cdc25-2 cell.

5. The method of claim 4, wherein the presence of a functional Ras protein in said cell is detected by cell growth at 33–37° C.

6. The method of claim 1, wherein said plasma membrane localization domain is a myristoylation signal.

7. A system for use in determining whether a first protein is capable of binding to a second protein, comprising:
 (a) a culture of cells incapable of activating a Ras protein;
 (b) a first nucleic acid vector, for inserting therein a DNA sequence encoding a first fusion protein which comprises a Ras protein mutated such that it cannot localize to the cell membrane and does not require an exchange factor and said first protein;

(c) a second nucleic acid vector, which may be the same or different than said first nucleic acid vector, for inserting therein a DNA sequence encoding a second fusion protein which comprises said second protein and a plasma membrane localization domain;

(d) reagents and devices for transfecting the cells with said first and said second nucleic acid;

(e) a monitoring arrangement for monitoring phenotypic Ras expression in said cells.

8. A kit comprising components of the system of claim 7.

9. The method of claim 2, wherein said cell is a yeast cell.

* * * * *